US010624348B2

(12) United States Patent
Gane et al.

(10) Patent No.: US 10,624,348 B2
(45) Date of Patent: Apr. 21, 2020

(54) ANTISEPTIC PRODUCT, PROCESS FOR PREPARING SAME AND ITS USE

(71) Applicant: Omya International AG, Oftringen (CH)

(72) Inventors: Patrick A. C. Gane, Rothrist (CH); Matthias Buri, Rothrist (CH); Simon Urwyler, Bern (CH); Anita Zumsteg, Meilen (CH); Joachim Glaubitz, Sins (CH)

(73) Assignee: OMYA INTERNATIONAL, Agoftringen (CH)

(*) Notice: Subject to any disclaimer, the term of this patent is extended or adjusted under 35 U.S.C. 154(b) by 0 days.

(21) Appl. No.: 15/325,236

(22) PCT Filed: Aug. 5, 2015

(86) PCT No.: PCT/EP2015/068040
§ 371 (c)(1),
(2) Date: Jan. 10, 2017

(87) PCT Pub. No.: WO2016/020428
PCT Pub. Date: Feb. 11, 2016

(65) Prior Publication Data
US 2017/0164616 A1 Jun. 15, 2017

(30) Foreign Application Priority Data
Aug. 7, 2014 (EP) .................................. 14180249

(51) Int. Cl.
A01N 59/08 (2006.01)
C08K 3/26 (2006.01)
C09D 5/16 (2006.01)
C09D 5/14 (2006.01)
A61K 31/555 (2006.01)
A01N 59/06 (2006.01)
A01N 55/02 (2006.01)
C08K 3/015 (2018.01)
A01N 59/00 (2006.01)
C08K 9/12 (2006.01)
A01N 25/08 (2006.01)
A01N 55/00 (2006.01)
A01N 59/04 (2006.01)

(52) U.S. Cl.
CPC ............ A01N 59/08 (2013.01); A01N 55/02 (2013.01); A01N 59/00 (2013.01); A01N 59/06 (2013.01); A61K 31/555 (2013.01); C08K 3/015 (2018.01); C08K 3/26 (2013.01); C09D 5/14 (2013.01); C09D 5/1618 (2013.01); C08K 9/12 (2013.01); C08K 2003/262 (2013.01); C08K 2003/265 (2013.01); C08K 2201/014 (2013.01); Y02A 50/473 (2018.01)

(58) Field of Classification Search
None
See application file for complete search history.

(56) References Cited

U.S. PATENT DOCUMENTS

| 4,086,297 | A | 4/1978 | Rei et al. |
| 4,655,815 | A | 4/1987 | Jakubowski |
| 4,663,359 | A | 5/1987 | Rei |
| 5,059,629 | A | 10/1991 | Patton et al. |
| 5,482,989 | A | 1/1996 | Koskiniemi |
| 5,496,398 | A | 3/1996 | Drew et al. |
| 6,569,229 | B1 | 5/2003 | Buri et al. |
| 2001/0009682 | A1 | 7/2001 | Whiteley |
| 2002/0022012 | A1 | 2/2002 | Cooper et al. |
| 2004/0023939 | A1 | 2/2004 | Buri et al. |
| 2005/0276897 | A1* | 12/2005 | Nover ............... C01F 11/18 426/594 |
| 2006/0065875 | A1 | 3/2006 | Buri et al. |
| 2006/0111410 | A1 | 5/2006 | Wachtler et al. |
| 2007/0191494 | A1 | 8/2007 | Buri et al. |
| 2008/0227766 | A1 | 9/2008 | Wunder et al. |
| 2009/0120327 | A1 | 5/2009 | Buri |
| 2013/0123369 | A1 | 5/2013 | De Maiuta et al. |
| 2013/0137778 | A1* | 5/2013 | Di Maiuta ............. A01N 37/04 514/770 |
| 2014/0000486 | A1 | 1/2014 | Buri et al. |

FOREIGN PATENT DOCUMENTS

| CN | 103518777 A | 1/2014 |
| EP | 2374353 A1 | 10/2011 |
| RU | 2010101936 A | 7/2011 |
| WO | 0185659 A1 | 11/2001 |
| WO | 02052941 A1 | 7/2002 |

(Continued)

OTHER PUBLICATIONS

Jeong et al. (Materials Transactions, vol. 50, No. 2 pp. 409 to 414) (Year: 2009).*
The International Search Report dated Sep. 30, 2015 for PCT/EP2015/068040.
The Written Opinion of International Searching Authority dated Sep. 30, 2015 for PCT/EP2015/068040.

Primary Examiner — Jeffrey T. Palenik
(74) Attorney, Agent, or Firm — Heslin Rothenberg Farley & Mesiti P.C.

(57) ABSTRACT

The present invention relates to a process for preparing an antiseptic product, an antiseptic product obtainable by the process, an antiseptic inorganic powder composition, an antiseptic polymer product as well as the use of one or more source of lithium ions in combination with one or more source of sodium ions for the preparation of an antiseptic product being effective against microbial contamination.

24 Claims, No Drawings

(56) References Cited

FOREIGN PATENT DOCUMENTS

| WO | 2004040979 A1 | 5/2004 |
| WO | 2006079911 A1 | 8/2006 |
| WO | 2007025917 A1 | 3/2007 |
| WO | 2007026004 A2 | 3/2007 |
| WO | 2009124871 A2 | 10/2009 |

* cited by examiner

ANTISEPTIC PRODUCT, PROCESS FOR PREPARING SAME AND ITS USE

CROSS-REFERENCE TO RELATED APPLICATIONS

This is a U.S. national phase of PCT Application No. PCT/EP2015/068040, filed Aug. 5, 2015, which claims priority to European Application No. 14180249.6, filed Aug. 7, 2014.

The present invention relates to a process for preparing an antiseptic product, an antiseptic product obtainable by the process, an antiseptic inorganic powder composition, an antiseptic polymer product as well as the use of one or more source of lithium ions in combination with one or more source of sodium ions for the preparation of an antiseptic product being effective against microbial contamination.

In practice, inorganic filler materials and especially calcium carbonate-containing filler materials are used extensively in processes to prepare paper, paint, rubber, adsorbing aids, cosmetics, coatings and plastics, among other applications. The aforementioned products are often subject to contamination by microorganisms such as fungi, yeasts, protozoa and/or aerobic and anaerobic bacteria when contacted with aqueous liquids such as water or aqueous liquids derived from animal or human beings such as urine, sweat, saliva, blood etc. Therefore, the manufacturer of such products usually takes measures for disinfecting and preserving them. For example, EP 1 139 741 describes aqueous suspensions or dispersions of minerals, fillers and/or pigments, containing a microbiocidal agent in the form of a solution and derivatives of phenol in partially neutralized form. WO 01/85659 mentions aqueous formulations containing one or more phenolates and at least one crystallization inhibitor that may be used to preserve mineral slurries. U.S. Pat. No. 5,496,398 relates to a process for the reduction of microorganisms in kaolin clay slurries by a combination of low temperature heat and reduced levels of a microbiocidal agent. WO 02/052941 describes biocide compositions for incorporation into paints, coating, plasters and plastics comprising at least one metal oxide and at least one metal salt. U.S. Pat. No. 4,655,815 mentions an antimicrobial composition comprising a formaldehyde donor. WO 2004/040979 A1 relates to synergic antimicrobial mixtures containing 1,2-benzisothiazolinone (BIT) and benzylhemiformal (BHF). The corresponding mixtures are used, for example, for slurries of pigments. WO 2007/025917 relates to a composition containing nanoparticulate silver and at least one additional constituent, selected from the group consisting of silver salts, nanoparticulate zinc oxide, chitosan and chitosan derivatives. US 2002/0022012 refers to a cationic dendrimer biocide-silver nanocomposite and methods for its use as a biocide. WO 2007/026004 A2 relates to a biocide composition comprising a combination of at least two biocide components, wherein the first component is embodied in the form of 1,2-benzisothiazolin-3-one and/or N-methyl-1,2-benzisothiazolin-3-one and/or N-methyl-1,2-benzisothiazolin-3-one and the other components are embodied in the form of a silver component, for example in the form of organic or inorganic silver salts, colloidal, particle silver or a silver oxide. Furthermore, US 2001/0009682 relates to disinfectant concentrates having improved biocidal activity which may contain an aldehyde such as glutaraldehyde, a glycol and a lithium based buffer. WO 2006/079911 describes a method of protection against microorganisms by increasing the OFF ion concentration of the suspension. US 2006/0111410 mentions a mixture comprising 1,2-benzisothiazolinone (BIT) and tetramethylol-acetylenediurea (TMAD) for protecting industrial materials and products against attack by microorganisms. U.S. Pat. No. 4,663,359 refers to a composition comprising a dry blend mixture of a porous thermoplastic resin powder and from 1 to 80 wt. % of a microbiocide based upon the weight of the composition. Preferred microbiocides are 10,10'-oxybisphenoxarsine; N-(trichloromethylthio)-4-cyclohexene-1,2-dicarboximide; 2,3,5,6-tetrachloro-4-(methylsulfonyl)pyridine; N-(2-methylnaphthyl)maleimide; and N-(trichloromethylthio)phthalimide. U.S. Pat. No. 5,059,629 refers to a biocidal foam product comprising a foam having incorporated therein a water insoluble thermoplastic copolymer consisting of an alpha olefin and an alpha, beta-ethylenically unsaturated carboxylic acid, said copolymer having at least one biocidal agent ionically bonded to said copolymer. U.S. Pat. No. 4,086,297 refers to a solid composition comprising a homogeneous mixture of a solid thermoplastic resin and from 1 to 80 weight % of at least one microbiocide which is insoluble in water. Suitable microbiocides include 10, 10'-oxybisphenoxarsine, N-(trichloromethylthio)-4-cyclo-hexene-1,2-dicarboximide, 2,3,5,6-tetrachloro-4-(methylsulfonyl) pyridine and N-(trichloromethylthio) phthalimide which is dispersed and/or solubilized in the resin. U.S. Pat. No. 5,482,989 relates to the use of calcium pyroborate to protect plastic materials from microbiological, growth, attack, or degradation. WO 2009/124871 A2 refers to a process for bacterial stabilizing aqueous preparations like e.g. calcium carbonate slurries and a composition which can be used for the biocidal treatment of such aqueous preparations.

However, the use of biocides is subject to continuously increasing limitations especially regarding the use of biocides having a potentially harmful effect on the environment or on humans and animals. Many biocides have a strong sensitizing or immune stimulation potential which forces industries to stop using certain biocides or to reduce the amounts used. Furthermore, antiseptic compounds typically have limited heat stability in pigment applications such as dry grinding of inorganic pigments in the presence of antiseptic compounds at increased temperature e.g. at above 100° C. and/or polymer applications such as in the preparation of polymer products e.g. by melt extrusion at temperatures of above 100° C. to 270° C. typically used for the preparation of films, fibres, containers and the like.

Therefore, there is a continuous need in the art for new antiseptic products and adequate processes for providing antiseptic products having sufficient preservation properties, easy handling, e.g. in powder form, heat stability at temperatures of above 100° C. without implementing substances causing reduced humans' or animals' health or environmental concerns.

Thus, it is an objective of the present invention to provide a process for preparing an antiseptic product having sufficient preservation properties. In particular, it is an objective of the present invention to provide a process for preparing an antiseptic product having sufficient preservation properties when it comes into contact with aqueous and/or organic liquids being microbial contaminated such as water or animals' and humans' liquids such as urine, sweat, blood, saliva and the like. A further objective of the present invention is to provide a process for preserving products that come into contact with water and/or organic solvents during their production or use such as paint and coating formulations, non-aqueous slurries, cosmetic formulations, creams, gels, fungicidal wall plaster formulations and the like as well as dry products such as films, plasters, diapers, tissues, coatings, adsorbing agents, plastic products and the like.

Another objective of the present invention is to provide a process for preparing an antiseptic product without implementing substances having a potentially harmful effect on the environment or a sensitizing or immune stimulation potential for human and animal beings. Another objective is to provide a process for preparing an antiseptic product providing a higher stability against heat or UV-light than most of the organic biocides typically used. Another objective is to provide an antiseptic product having sufficient preservation properties when it comes into contact with aqueous and/or organic liquids being microbial contaminated such as water or animals' and humans' liquids such as urine, sweat, blood, saliva and the like. Another objective of the present invention is to provide an antiseptic product without implementing substances having a potentially harmful effect on the environment or a sensitizing or immune stimulation potential for human and animal beings. A further objective is to provide an antiseptic product providing a higher stability against heat or UV-light than most of the organic biocides typically used.

These and other objectives of the present invention can be solved by a process, an antiseptic product, an antiseptic inorganic powder composition, an antiseptic polymer product and the use of one or more source of lithium ions in combination with one or more source of sodium ions for the preparation of an antiseptic product being affective against microbial contamination as described in the present invention and defined in the claims.

According to one aspect of the present application, a process for preparing an antiseptic product is provided. The process comprises the steps of:
a) providing at least one inorganic filler material,
b) providing one or more source of lithium ions,
c) providing one or more source of sodium ions,
d) combining the at least one inorganic filler material of step a) with the one or more source of lithium ions of step b) in an amount such that the total amount of lithium ions in the final antiseptic product is from 20 to 60 000 ppm, based on the total weight of the antiseptic product,
e) combining the at least one inorganic filler material of step a) with the one or more source of sodium ions of step c) in an amount such that the total amount of sodium ions in the final antiseptic product is from 20 to 20 000 ppm, based on the total weight of the antiseptic product, and
wherein process steps d) and e) are carried out simultaneously, or separately in any order and wherein the molar ratio of sodium ions:lithium ions (Na:Li) in the antiseptic product is from 1:1 to 1:10 and the moisture content of the antiseptic product is <15.0 wt.-%, based on the total weight of the antiseptic product.

EP 2 374 353 refers to a process for preserving an aqueous preparation of mineral material. It is described that one or more sources of lithium ions and one or more sources of sodium and/or potassium and/or magnesium ions are added to an aqueous preparation of at least one mineral material.

Indeed, it is a remarkable advantage of the present invention that the one or more source of lithium ions and the one or more source of sodium ions can be combined, preferably as dry materials, and that this mixture can be implemented in a great variety of liquid as well as dry products and thus providing antiseptic properties. Furthermore, it was surprisingly found out that a mixture comprising one or more source of lithium ions in a specific molar ratio with one or more source of sodium ions has antiseptic properties when it comes into contact with moisture.

In accordance with the present invention, the lithium ions of the one or more source of lithium ions in combination with the sodium ions of the one or more source of sodium ions may be regarded as a substance having antimicrobial activity or an antiseptic effect. Thus, when subsequently reference is made to a substance having antimicrobial activity or antiseptic effect, the lithium ions of the one or more source of lithium ions in combination with the sodium ions of the one or more source of sodium ions in a specific molar ratio are meant.

In the meaning of the present invention, an "antiseptic product" or a product having "antimicrobial activity", "an antiseptic effect" or "being affective against microbial contamination" refers to a product being effective against at least one strain of bacteria and/or at least one strain of yeast and/or at least one strain of mould. The term "effective" refers to the ability of the antiseptic product to reduce the total number and/or to prevent or reduce the growth or accumulation of at least one strain of bacteria and/or at least one strain of yeast and/or at least one strain of mould in the antiseptic product or on the antiseptic product surface.

According to the present invention, the wording "reduce the total number" means that a reduction in the total number of at least one strain of bacteria and/or at least one strain of yeast and/or at least one strain of mould is observed in the antiseptic product or on the antiseptic product surface having antimicrobial activity compared to the product or on the product surface without having antimicrobial activity. The total number of at least one strain of bacteria and/or at least one strain of yeast and/or at least one strain of mould can be measured using standard microbiological techniques known to the skilled person and can be measured, for example, by plate-out on a tryptic soy agar (TSA) as described in the example section.

According to the present invention, the wording "prevent or reduce the growth or accumulation" means that no significant growth or accumulation of at least one strain of bacteria and/or at least one strain of yeast and/or at least one strain of mould is observed in the antiseptic product or on the antiseptic product surface. A "significant growth or accumulation" of the at least one strain of bacteria and/or at least one strain of yeast and/or at least one strain of mould is observed if the difference, i.e. the growth of the of the at least one strain of bacteria and/or at least one strain of yeast and/or at least one strain of mould is greater than the error associated with the measurement technique when tested within one-week and measured by plate-out on a tryptic soy agar (TSA), where the plates are incubated at 30° C. and evaluated after 48 hours, according to the bacterial count method described in the example section herein.

According to the present invention, the lithium and sodium ion content can be evaluated in liquid formulations by filtering off the solids in the formulation by membrane filtration (pore size of 0.2 microns) and/or, pressure filtration and measuring the lithium ion content in the filtrate by ion chromatography and/or inductive coupled plasma optical atomic emission spectroscopy (ICP-OES). The lithium and sodium content in dry products can be measured by solubilisation of the dry product by acidic decomposition and quantification of the ions by ICP-OES.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Where an indefinite or definite article is used when referring to a singular noun, e.g. "a", "an" or "the", this includes a plural of that noun unless something else is specifically stated.

Terms like "obtainable" or "definable" and "obtained" or "defined" are used interchangeably. This e.g. means that, unless the context clearly dictates otherwise, the term "obtained" does not mean to indicate that, e.g. an embodiment must be obtained by e.g. the sequence of steps following the term "obtained" even though such a limited understanding is always included by the terms "obtained" or "defined" as a preferred embodiment.

Furthermore, the present invention refers in another aspect to an antiseptic product, preferably a paint or coating formulation, non-aqueous slurry, cosmetic formulation, cream, gel, fungicidal wall plaster formulation, film, plaster, diaper, tissue, plastic product or adsorbing agent for aqueous and/or organic fluids, obtainable by the process.

According to a further aspect of the present invention, an antiseptic inorganic powder composition is provided. The antiseptic inorganic powder composition comprising
 a) at least one inorganic filler material as defined herein,
 b) 20 to 20 000 ppm of one or more source of sodium ions, based on the total weight of the antiseptic inorganic powder composition, and
 c) 20 to 60 000 ppm of one or more source of lithium ions, based on the total weight of the antiseptic inorganic powder composition,
wherein the molar ratio of sodium ions:lithium ions (Na:Li) in the antiseptic inorganic powder composition is from 1:1 to 1:10 and the moisture content of the antiseptic inorganic powder composition is <15.0 wt.-%, based on the total weight of the antiseptic inorganic powder composition.

According to one embodiment of the present antiseptic inorganic powder composition, the moisture content of the antiseptic inorganic powder composition is ≤5.0 wt.-%, preferably ≤1.0 wt.-%, more preferably ≤0.2 wt.-%, and most preferably from 0.03 to 0.15 wt.-%, based on the total weight of the antiseptic inorganic powder composition.

According to another embodiment of the present antiseptic inorganic powder composition, the antiseptic inorganic powder composition has hydrophobic surface properties.

According to another aspect of the present invention, an antiseptic polymer product is provided. The antiseptic polymer product comprising
 a) an organic polymer composition comprising at least one organic polymer resin being selected from the group consisting of a thermoplast, duroplast, elastomer and mixtures thereof,
 b) 20 to 20 000 ppm of one or more source of sodium ions, based on the total weight of the antiseptic polymer composition,
 c) 20 to 60 000 ppm of one or more source of lithium ions, based on the total weight of the antiseptic polymer composition, and
 d) optionally at least one inorganic filler material as defined herein,
wherein the molar ratio of sodium ions:lithium ions (Na:Li) in the antiseptic polymer product is from 1:1 to 1:10 and the moisture content of the antiseptic polymer product is ≤1.0 wt.-%, based on the total weight of the antiseptic polymer product.

According to one embodiment of the present antiseptic polymer product, the at least one organic polymer resin is selected from the group comprising halogenated polymer resins, styrenic resins, acrylic resins, polyolefines, polycarbonate resins, polyester resins, polyurethane resins, polyamide resins, biopolymers, copolymers, polyvinyl chlorides, polylactides, acrylonitrile butadiene styrenes, synthetic rubbers, natural rubbers and mixtures thereof.

According to another embodiment of the present antiseptic polymer product, the at least one inorganic filler material is the carrier for the sodium ion and/or lithium ion source.

According to yet another embodiment of the present antiseptic polymer product and/or the antiseptic inorganic powder composition, the one or more source of sodium ions and/or lithium ions are/is a corresponding carbonate salt(s).

According to still another aspect of the present invention, the use of one or more source of lithium ions in combination with one or more source of sodium ions for the preparation of an antiseptic product being effective against microbial contamination is provided. The antiseptic product comprises the
 a) one or more source of lithium ions in an amount such that the total amount of lithium ions in the antiseptic product is from 20 to 60 000 ppm, based on the total weight of the antiseptic product, and
 b) one or more source of sodium ions in an amount such that the total amount of sodium ions in the antiseptic product is from 20 to 20 000 ppm, based on the total weight of the antiseptic product.

According to one embodiment of the present use, no further biocide is employed.

According to one embodiment of the present process, the at least one inorganic filler material of step a) is selected from the group consisting of ground natural calcium carbonate (GCC), precipitated calcium carbonate (PCC), modified calcium carbonate (MCC), kaolin, kaolinitic clay, calcined kaolinitic clay, talc, calcium sulfate, quartz, attapulgite, montmorillonite, diatomaceous earth, finely divided silica, aluminium oxide, aluminium hydroxide, silicates, pumice, sepiolite, dolomite, mica, titanium dioxide, and mixtures thereof, and more preferably from the group consisting of ground natural calcium carbonate (GCC), such as marble, limestone, chalk or mixtures thereof, modified calcium carbonate (MCC), precipitated calcium carbonate (PCC), dolomite, kaolin, kaolinitic clay, calcined kaolinitic clay and mixtures thereof.

According to another embodiment of the present process, the at least one inorganic filler material is combined with the one or more source of lithium ions in step d) in an amount such that the total amount of lithium ions in the antiseptic product is from 20 to 30 000 ppm, based on the total weight of the antiseptic product.

According to yet another embodiment of the present process, the at least one inorganic filler material is combined with the one or more source of sodium ions in step e) in an amount such that the total amount of sodium ions in the antiseptic product is from 20 to 10 000 ppm, based on the total weight of the antiseptic product.

According to one embodiment of the present process, process steps d) and e) are carried out simultaneously, preferably process steps d) and e) are carried out in that the at least one inorganic filler material is combined with a blend consisting of the one or more source of lithium ions and the one or more source of sodium ions.

According to another embodiment of the present process, the process further comprises step f) of i) dry grinding the mixture of the at least one inorganic filler material, the one or more source of lithium ions and the one or more source of sodium ions obtained during and/or after step d) and e), and/or ii) contacting the mixture of the at least one inorganic filler material, the one or more source of lithium ions and the one or more source of sodium ions obtained after step d) and e) with water and/or at least one dispersing agent, or iii) contacting the mixture of the at least one inorganic filler material, the one or more source of lithium ions and the one or more source of sodium ions obtained after step d) and e) with an organic polymer composition comprising at least one organic polymer resin being selected from the group consisting of a thermoplast, duroplast, elastomer and mixtures thereof and subjecting the obtained composition to conditions under which it is converted into an antiseptic polymer product.

According to yet another embodiment of the present process, the at least one inorganic filler material after step d) and/or e) has a volume median diameter $d_{50}$ value from 0.5 to 25.0 μm, preferably from 0.7 to 5.0 μm, more preferably from 1.0 to 4.0 μm and most preferably from 1.5 to 3.5 μm, measured according to the dry laser diffraction method.

According to one embodiment of the present process, no further biocide in addition to the antiseptic effect formed by combining the one or more source of lithium ions with the one or more source of sodium ions is employed in the antiseptic product.

According to another embodiment of the present process, the antiseptic product is a non-aqueous slurry, paint or coating formulation, cosmetic formulation, cream, gel, fungicidal wall plaster formulation, film, plaster, diaper, tissue, plastic product or adsorbing agent for aqueous and/or organic fluids.

According to yet another embodiment of the present process, the antiseptic product has an antiseptic effect against at least one strain of bacteria and/or at least one strain of mould and/or at least one strain of yeast, preferably the at least one strain of bacteria is selected from the group consisting of *Escherichia* sp., *Staphylococcus* sp., *Thermus* sp., *Propionibacterium* sp., *Rhodococcus* sp., *Pannninobacter* sp., *Caulobacter* sp., *Brevundimonas* sp., *Asticcacaulis* sp., *Sphingomonas* sp., *Rhizobium* sp., *Ensifer* sp., *Bradyrhizobium* sp., *Tepidimonas* sp., *Tepidicella* sp., *Aquabacterium* sp., *Pelomonas* sp., *Alcaligenis* sp., *Achromobacter* sp., *Ralstonia* sp., *Limnobacter* sp., *Massilia* sp., *Hydrogenophaga* sp., *Acidovorax* sp., *Curvibacter* sp., *Delftia* sp., *Rhodoferax* sp., *Alishewanella* sp., *Stenotrophomonas* sp., *Dokdonella* sp., *Methylosinus* sp., *Hyphomicrobium* sp., *Methylosulfomonas* sp., *Methylobacteria* sp., *Pseudomonas* sp. *Enterococcus* sp., *Myroides* sp., *Burkholderia* sp., *Alcaligenes* sp. and mixtures thereof and/or the at least one strain of mould is selected from the group comprising of *Acremonium* sp., *Alternaria* sp., *Aspergillus* sp., *Cladosporium* sp., *Fusarium* sp., *Mucor* sp., *Penicillium* sp., *Rhizopus* sp., *Stachybotrys* sp., *Trichoderma* sp., *Dematiaceae* sp., *Phoma* sp., *Eurotium* sp., *Scopulariopsis* sp., *Aureobasidium* sp., *Monilia* sp., *Botrytis* sp., *Stemphylium* sp., *Chaetomium* sp., *Mycelia* sp., *Neurospora* sp., *Ulocladium* sp., *Paecilomyces* sp., *Wallemia* sp., *Curvularia* sp., and mixtures thereof and/or the at least one strain of yeast is selected from the group comprising *Saccharomycotina, Taphrinomycotina, Schizosaccharomycetes, Basidiomycota, Agaricomycotina, Tremellomycetes, Pucciniomycotina, Microbotryomycetes, Candida* sp. such as *Candida albicans, Candida tropicalis, Candida stellatoidea, Candida glabrata, Candida krusei, Candida guilliermondii, Candida viswanathii, Candida lusitaniae* and mixtures thereof *Yarrowia* sp. such as *Yarrowia lipolytica, Cryptococcus* sp. such as *Cryptococcus gattii* and *Cryptococcus neofarmans, Zygosaccharomyces* sp., *Rhodotorula* sp. such as *Rhodotorula mucilaginosa*, and mixtures thereof, and more preferably the at least one strain of bacteria is selected from the group consisting of *Escherichia coli, Staphylococcus aureus, Pseudomonas putida, Pseudomonas mendocina, Pseudomonas oleovorans, Pseudomonas fluorescens, Pseudomonas alcaligenes, Pseudomonas pseudoalcaligenes, Pseudomonas entomophila, Pseudomonas syringae, Methylobacterium extorquens, Methylobacterium radiotolerants, Methylobacterium dichloromethanicum, Methylobacterium organophilu, Hyphomicrobium zavarzini, Enterococcus faecalis, Myroides odoratus, Pseudomonas aeruginosa, Pseudomonas orizyhabitans, Burkholderia cepacia, Alcaligenes faecalis* and *Sphingomonas paucimobilis* and mixtures thereof.

As set out above, the inventive process for preparing an antiseptic product comprises the steps a), b), c), d) and e). In the following, it is referred to further details of the present invention and especially the foregoing steps of the inventive process for preparing an antiseptic product. Those skilled in the art will understand that many embodiments described herein can be combined or applied together.

Characterisation of Step a): Provision of at Least One Dry Inorganic Filler Material According to step a) of the process of the present invention, at least one inorganic filler material is provided.

The term "at least one" inorganic filler material in the meaning of the present invention means that the inorganic filler material comprises, preferably consists of, one or more inorganic filler materials.

In one embodiment of the present invention, the at least one inorganic filler material comprises, preferably consists of, inorganic filler material. Alternatively, the at least one inorganic filler material comprises, preferably consists of, two or more inorganic filler materials. For example, the at least one inorganic filler material comprises, preferably consists of, two or three inorganic filler materials. Preferably, the at least one inorganic filler material comprises, preferably consists of, one inorganic filler material.

In one embodiment of the present invention, the at least one inorganic filler material is selected from the group consisting of ground natural calcium carbonate (GCC), precipitated calcium carbonate (PCC), modified calcium carbonate (MCC), kaolin, kaolinitic clay, calcined kaolinitic clay, talc, calcium sulfate, quartz, attapulgite, montmorillonite, diatomaceous earth, finely divided silica, aluminium oxide, aluminium hydroxide, silicates, pumice, sepiolite, dolomite, mica, titanium dioxide, and mixtures thereof.

For example, the at least one inorganic filler material is selected from the group consisting of ground natural calcium carbonate (GCC), such as marble, limestone, chalk or mixtures thereof, modified calcium carbonate (MCC), precipitated calcium carbonate (PCC), dolomite, kaolin, kaolinitic clay, calcined kaolinitic clay and mixtures thereof.

Preferably, the at least one inorganic filler material comprises, more preferably consists of, ground natural calcium carbonate (GCC), such as marble, limestone, chalk or mixtures thereof, and/or precipitated calcium carbonate (PCC).

"Ground calcium carbonate" (GCC) in the meaning of the present invention is a calcium carbonate obtained from natural sources, such as limestone, marble or chalk, and processed through a treatment such as grinding, screening and/or fractionizing by wet and/or dry, for example by a cyclone or classifier.

"Precipitated calcium carbonate" (PCC) in the meaning of the present invention is a synthesized material, generally obtained by precipitation following reaction of carbon dioxide and lime in an aqueous environment or by precipitation of a calcium and carbonate ion source in water.

"Modified calcium carbonate" (MCC) in the meaning of the present invention may feature a natural ground or precipitated calcium carbonate with an internal structure modification or a surface-reaction product. According to a preferred embodiment of the present invention, the modified calcium carbonate is a surface-reacted calcium carbonate.

"Dolomite" and dolomite containing marble in the meaning of the present invention is a carbonatic calcium-magnesium-mineral having the chemical composition of CaMg$(CO_3)_2$ ("$CaCO_3.MgCO_3$") or a blend of CaMg$(CO_3)_2$ and $CaCO_3$.

"Clay" refers to crystalline or amorphous small particles of mainly hydrous silicates of aluminum, sometimes with magnesium, calcium and/or iron substitution for all or a part of the aluminium. The main groups of clay minerals are: kaolinite, the main constituent of kaolin; halloysite; illite; montmorillonite and vermiculite. The term "kaolinitic clay" used herein refers to soft white clay that is composed mainly of the mineral kaolinite.

"Kaolin" is especially used in the paper industry, which uses them to coat and fill papers and boards and improves some of the optical properties of the final product, such as gloss, opacity or brightness. However, kaolin based products include paints, agricultural compositions, fibre glass products, polymer and rubber compositions, ceramic applications, catalyst supports, pharmaceuticals, cosmetics, adhesives, filter aids, and many more.

The natural ground calcium carbonate and/or modified calcium carbonate (MCC) and/or precipitated calcium carbonate (PCC) may additionally be surface treated, for example with fatty acids such as stearic acid and corresponding calcium salts.

The at least one inorganic filler material is preferably at least one dry inorganic filler material.

The term at least one "dry" inorganic filler material refers to filler material particles having a total moisture content of <15.0 wt.-%, preferably ≤5.0 wt.-%, more preferably ≤1.0 wt.-%, even more preferably ≤0.5 wt.-% and most preferably ≤0.3 wt.-%, based on the total weight of the at least one inorganic filler material.

The at least one inorganic filler material may have a particle size distribution as conventionally employed for the material(s) involved in the type of products to be produced. In general, 90.0 vol.-% of the particles will have an esd (equivalent spherical diameter as measured by the well-known dry laser diffraction method, preferably by using Mastersizer 3000 including an Aero S dry powder disperser from Malvern Instruments Ltd., United Kingdom) of less than 11.0 micrometres (μm). Coarse inorganic filler materials may have a particle esd generally (i.e., at least 90.0 vol.-%) in the range of 3.0 to 11.0 microns. Fine dry inorganic filler materials may have a particle esd generally less than 3.0 μm, e.g. 50.0 to 99.0 vol.-% less than 3.0 μm and preferably 60.0 to 90.0 vol.-% less than 3.0 μm, measured according to the dry laser diffraction method, preferably by using Mastersizer 3000 including an Aero S dry powder disperser from Malvern Instruments Ltd., United Kingdom.

It is preferred that the at least one inorganic filler material has a volume median particle size $d_{50}$ value of from 0.5 to 25.0 μm, preferably from 0.7 to 5.0 μm, more preferably from 1.0 to 4.0 μm and most preferably from 1.5 to 3.5 μm, measured according to the dry laser diffraction method, preferably by using Mastersizer 3000 including an Aero S dry powder disperser from Malvern Instruments Ltd., United Kingdom.

Throughout the present document, the "particle size" of a pigment particle is described by its distribution of particle sizes. The value $d_x$ represents the diameter relative to which x % by volume of the particles have diameters less than $d_x$. This means that the $d_{20}$ value is the particle size at which 20.0 vol.-% of all particles are smaller, and the $d_{75}$ value is the particle size at which 75.0 vol.-% of all particles are smaller. The $d_{50}$ value is thus the volume median particle size, i.e. 50.0 vol.-% of all particle grains are bigger or smaller than this particle size. For the purpose of the present invention the particle size is specified as volume median particle size $d_{50}$ unless indicated otherwise. For determining the volume median particle size $d_{50}$ value, the dry laser diffraction method, preferably a Mastersizer 3000 including an Aero S dry powder disperser from Malvern Instruments Ltd., United Kingdom, can be used.

Characterisation of Step b): Providing One or More Dry Source of Lithium Ions

According to step b) of the process of the present invention, one or more source of lithium ions is provided.

In one embodiment of the present invention, the one or more source of lithium ions comprises, preferably consists of, one source of lithium ions. Alternatively, the one or more source of lithium ions comprises, preferably consists of, two or more sources of lithium ions. For example, the one or more source of lithium ions comprises, preferably consists of, two or three sources of lithium ions. Preferably, the one or more source of lithium ions comprises, preferably consists of, one source of lithium ions.

The term one or more "source of lithium ions" in the meaning of the present invention refers to a compound that comprises lithium ions, i.e. lithium cations. Preferably, the term "source of lithium ions" includes lithium ions as part of a salt, e.g. in a crystalline or amorphous form.

It is appreciated that the one or more source of lithium ions provided in step b) of the instant process may be a lithium ion-comprising compound that is soluble in water. Thus, the one or more source of lithium ions is preferably one or more "water-soluble" lithium ions source.

The term "water-soluble" lithium ion source or "soluble in water" in the meaning of the present invention refers to systems in which at least a part of the lithium ion source may form a solution with water, i.e. at least a part of the particles of the at least one source of lithium ions are dissolved in the solvent.

In one embodiment of the present invention, the one or more source of lithium ions is preferably provided in the form of one or more lithium salt. Preferably the anionic group of the one or more lithium salt is selected from the group comprising carbonate, halide such as chloride, fluoride, bromide or iodide, sulphate, hydrogen sulphate, citrate, $C_6$ to $C_{24}$ fatty acid such as maleate, stearate and mixtures thereof. In particular, the one or more lithium salt is selected from lithium carbonate, lithium halide such as lithium chloride, lithium fluoride, lithium bromide, lithium iodide, lithium sulphate, lithium hydrogen sulphate, lithium citrate, lithium salt of a $C_6$ to $C_{24}$ fatty acid such as lithium maleate, lithium stearate, and mixtures thereof.

Additionally or alternatively, the one or more source of lithium ions can be provided as a mono-, bi- or trivalent source of lithium ions. Preferably, the one or more source of lithium ions is provided as a mono- or bivalent source of lithium ions. More preferably, the one or more source of lithium ions is provided as a bivalent source of lithium ions.

It is appreciated that lithium carbonate and/or lithium stearate, more preferably lithium carbonate, are preferred as the one or more lithium salt, i.e. the one or more source of lithium ions of the present invention.

The one or more source of lithium ions is preferably one or more dry source of lithium ions.

The term one or more "dry" source of lithium ions refers to a lithium ions source having a total moisture content of <15.0 wt.-%, preferably ≤5.0 wt.-%, more preferably ≤1.0 wt.-%, even more preferably ≤0.5 wt.-% and most preferably ≤0.3 wt.-%, based on the total weight of the one or more source of lithium ions. In one embodiment of the present invention, said one or more source of lithium ions is provided in step b) in an amount such that the total amount of lithium ions in the final antiseptic product is from 20 to 60 000 ppm, based on the total weight of the antiseptic product. Preferably, the one or more source of lithium ions is provided in step b) in an amount such that the total amount of lithium ions in the final antiseptic product is from 20 to 30 000 ppm, based on the total weight of the antiseptic product. More preferably, the one or more source of lithium ions is provided in step b) in an amount such that the total amount of lithium ions in the final antiseptic product is from 20 to 10 000 ppm, based on the total weight of the antiseptic product.

It is to be noted that the aforementioned figures reflect the amount of lithium ions being added to the inorganic filler material comprising product via the instant process, and do not cover any lithium ions which may naturally be present in the antiseptic product. However, the amount of naturally occurring lithium ions in e.g. a calcium carbonate slurry or plastic product usually is negligible and well below 20 ppm, based on the inorganic filler material content of the respective product.

The optimum amount to be employed within the defined ranges can be easily determined by preliminary tests and test series on a laboratory scale and by supplementary operational tests.

Characterisation of Step c): Providing One or More Source of Sodium Ions

According to step c) of the process of the present invention, one or more source of sodium ions is provided.

In one embodiment of the present invention, the one or more source of sodium ions comprises, preferably consists of, one source of sodium ions. Alternatively, the one or more source of sodium ions comprises, preferably consists of, two or more sources of sodium ions. For example, the one or more source of sodium ions comprises, preferably consists of, two or three sources of sodium ions. Preferably, the one or more source of sodium ions comprises, preferably consists of, one source of sodium ions.

The term one or more "source of sodium ions" in the meaning of the present invention refers to a compound that comprises sodium ions, i.e. sodium cations. Preferably, the term "source of sodium ions" includes sodium as part of a salt, e.g. in a crystalline or amorphous form.

It is appreciated that the one or more source of sodium ions provided in step c) of the instant process may be a sodium ion-comprising compound that is soluble in water. Thus, the one or more source of sodium ions is preferably one or more "water-soluble" sodium ions source.

The term "water-soluble" sodium ion source or "soluble in water" in the meaning of the present invention refers to systems in which at least a part of the sodium ion source may form a solution with water, i.e. at least a part of the particles of the at least one source of sodium ions are dissolved in the solvent.

In one embodiment of the present invention, the one or more source of sodium ions is preferably provided in the form of one or more sodium salt. Preferably the anionic group of the one or more sodium salt is selected from the group comprising carbonate, chloride, citrate, $C_6$ to $C_{24}$ fatty acid such as maleate, stearate and mixtures thereof. In particular, the one or more sodium salt is selected from sodium carbonate, sodium chloride, sodium citrate, sodium $C_6$ to $C_{24}$ fatty acid such as sodium maleate, sodium stearate, and mixtures thereof.

It is appreciated that sodium carbonate and/or sodium chloride, more preferably sodium carbonate, are preferred as the one or more sodium salt, i.e. the one or more source of sodium ions of the present invention.

Additionally or alternatively, the one or more source of sodium ions can be provided as a mono-, bi- or trivalent source of sodium ions. Preferably, the one or more source of sodium ions is provided as a mono- or bivalent source of sodium ions. More preferably, the one or more source of sodium ions is provided as a bivalent source of sodium ions.

In one embodiment of the present invention, the one or more source of sodium ions and the one or more source of lithium ions are provided as separate sources, i.e. the one or more source of sodium ions and the one or more source of lithium ions are not provided in form of one source comprising sodium and lithium ions. That is to say, the one or more source of sodium ions and the one or more source of lithium ions are provided as two or more sources, one or more source comprising sodium ions and one or more source comprising lithium ions.

The one or more source of sodium ions is preferably one or more dry source of sodium ions.

The term one or more "dry" source of sodium ions refers to a sodium ions source having a total moisture content of <15.0 wt.-%, preferably ≤5.0 wt.-%, more preferably ≤1.0 wt.-%, even more preferably ≤0.5 wt.-% and most preferably ≤0.3 wt.-%, based on the total weight of the one or more source of sodium ions.

In one embodiment of the present invention, said one or more source of sodium ions is provided in step c) in an amount such that the total amount of sodium ions in the final antiseptic product is from 20 to 20 000 ppm, based on the total weight of the antiseptic product. Preferably, the one or more source of sodium ions is provided in step c) in an amount such that the total amount of sodium ions in the final antiseptic product is from 20 to 10 000 ppm, based on the total weight of the antiseptic product. More preferably, the one or more source of sodium ions is provided in step c) in an amount such that the total amount of sodium ions in the final antiseptic product is from 20 to 5 000 ppm, based on the total weight of the antiseptic product.

It is to be noted that the aforementioned figures reflect the amount of sodium ions being added to the inorganic filler material comprising product via the instant process, and do not cover any sodium ions which may naturally be present in the product.

The optimum amount to be employed within the defined ranges can be easily determined by preliminary tests and test series on a laboratory scale and by supplementary operational tests.

Characterisation of Steps d) and e): Combining the at Least One Inorganic Filler Material with the One or More Source of Lithium Ions and the One or More Source of Sodium Ions According to step d) of the process of the present invention, the at least one inorganic filler material of step a) is combined with the one or more source of lithium ions of step b). It is one requirement of the instant process that the at least one inorganic filler material is combined with the one or more source of lithium ions in an amount such that the total amount of lithium ions in the final antiseptic product is from 20 to 60 000 ppm, based on the total weight of the antiseptic product.

In one embodiment of the present invention, the at least one inorganic filler material is combined with the one or more source of lithium ions in an amount such that the total amount of lithium ions in the final antiseptic product is from 20 to 30 000 ppm and preferably from 20 to 10 000 ppm, based on the total weight of the antiseptic product.

According to step e) of the process of the present invention, the at least one inorganic filler material of step a) is combined with the one or more source of sodium ions of step c). It is one requirement of the instant process that the at least one inorganic filler material is combined with the one or more source of sodium ions in an amount such that the total amount of sodium ions in the final antiseptic product is from 20 to 20 000 ppm, based on the total weight of the antiseptic product.

In one embodiment of the present invention, the at least one inorganic filler material is combined with the one or more source of sodium ions in an amount such that the total amount of sodium ions in the final antiseptic product is from 20 to 10 000 ppm and preferably from 20 to 5 000 ppm, based on the total weight of the antiseptic product.

It is appreciated that said one or more source of lithium ions of step b) and said one or more source of sodium ions of step c) can be added to the at least one inorganic filler material of step a) in any order. Thus, they can be added simultaneously or separately in any order to the at least one inorganic filler material, in a manner known by the skilled person.

In one embodiment of the present invention, process steps d) and e) are carried out simultaneously. For example, process steps d) and e) are carried out in that the at least one inorganic filler material is combined with a blend consisting of the one or more source of lithium ions and the one or more source of sodium ions. That is to say, said one or more source of lithium ions of step b) and said one or more source of sodium ions of step c) may be pre-mixed prior to addition to said at least one inorganic filler material of step a).

In an alternative embodiment, said one or more source of lithium ions of step b) and said one or more source of sodium ions of step c) are added separately. For example, the one or more source of lithium ions of step b) can be added to the at least one dry inorganic filler material of step a) prior the one or more source of sodium ions of step c). Alternatively, the one or more source of lithium ions of step b) can be added to the at least one dry inorganic filler material of step a) after the one or more source of sodium ions of step c).

It is preferred that the one or more dry source of lithium ions of step b) and the one or more dry source of sodium ions of step c) are added to the at least one inorganic filler material of step a) under mixing.

It is appreciated that process steps d) and e) can be repeated one or more times.

It is one requirement of the instant invention that the sodium ions and the lithium ions are provided in a specific molar ratio in order to achieve an antiseptic effect in the final antiseptic product. Accordingly, it is required that the molar ratio of sodium ions:lithium ions (Na:Li) in the antiseptic product is from 1:1 to 1:10. For example, the molar ratio of sodium ions:lithium ions (Na:Li) in the antiseptic product is from 1:1.1 to 1:10, preferably from 1:1.5 to 1;10 and most preferably from 1:2 to 1:8.

It is further appreciated that the antiseptic product obtained by the instant process has a moisture content of <15.0 wt.-%, based on the total weight of the antiseptic product. For example, the moisture content of the antiseptic product is ≤5.0 wt.-%, preferably ≤1.0 wt.-%, more preferably ≤0.2 wt.-%, and most preferably from 0.03 to 0.15 wt.-%, based on the total weight of the antiseptic product.

In one embodiment, the at least one inorganic filler material after step d) and/or e) has a volume median diameter $d_{50}$ value from 0.5 to 25.0 µm, preferably from 0.7 to 5.0 µm, more preferably from 1.0 to 4.0 µm and most preferably from 1.5 to 3.5 µm, measured according to the dry laser diffraction method, preferably by using Mastersizer 3000 including an Aero S dry powder disperser from Malvern Instruments Ltd., United Kingdom.

Additional Process Steps

In addition to the one or more source of lithium ions and the one or more source of sodium ions, conventional biocides may additionally be added to the at least one inorganic filler material of step a). However, in a more preferred embodiment, no biocide in addition to the antiseptic effect formed by combining the one or more source of lithium ions with the one or more source of sodium ions is employed in the process of the present invention.

Accordingly, it is appreciate that no further biocide in addition to the antiseptic effect formed by combining the one or more source of lithium ions with the one or more source of lithium ions is employed in the antiseptic product having antimicrobial activity. In the less preferred embodiment where a conventional further biocide is employed, it is preferred that said further biocide is a disinfectant, in which case it is most preferred that said disinfectant is added prior to the one or more source of lithium ions and the one or more source of sodium ions. Said disinfectant may additionally be dosed following addition of the one or more source of lithium ions and the one or more source of sodium ions.

The further biocide is preferably selected from the group comprising phenols, halogenated phenols, halogen-containing compounds, halogen-releasing compounds, isothiazolinones, aldehyde-containing compounds, aldehyde-releasing compounds, guanidines, sulphones, thiocyanates, pyrithiones, antibiotics such as β-lactam antibiotics, quaternary ammonium salts, peroxides, perchlorates, amides, amines, heavy metals, biocidal enzymes, biocidal polypeptides, azoles, carbamates, glyphosates, sulphonamides and mixtures thereof.

The phenol biocide is preferably 2-phenylphenol (OPP) (CAS NO 90-43-7) and/or 2-phenylphenol (OPP) in the form of the alkali metal salt such as the sodium salt (CAS NO 132-27-4) or potassium salt (CAS NO 13707-65-8).

The halogenated phenol biocide of the present invention is preferably 4-chloro-3-methylphenol (CAS NO 59-50-7) and/or 4-chloro-2-methylphenol (CAS NO 1570-64-5).

The biocide being a halogen-containing or halogen-releasing compound is preferably selected from bronopol (CAS NO 52-51-7), bronidox (CAS NO 30007-47-7), 2,2-dibrom-3-nitrilpropionamid (DBNPA) (CAS NO 10222-01-2), 1,2-dibromo-2,4-dicyanobutane (CAS NO 35691-65-7), monochloroamine (CAS NO 10599-90-3), ammonium bromide (CAS NO 12124-97-9), calcium hypochlorite (CAS NO 7778-54-3), iodine (CAS NO 7553-56-2), tri-iodide (CAS NO 14900-04-0), potassium iodate (CAS NO 7758-05-6) and mixtures thereof.

In accordance with the present invention, a "halogen-containing biocide" refers to a biocide which has one or more halogen-groups. In accordance with the present invention, a "halogen-releasing biocide" refers to a compound which is able to release or transfer a halogen group.

The isothiazolinone biocide is preferably selected from the group comprising isothiazolinone (IT) (CAS NO 1003-07-2), benzisothiazolinone (BIT) (CAS NO 2634-33-5), 5-chloro-2-methyl-2H-isothiazolin-3-one (CMIT) (CAS NO 26172-55-4), 2-methyl-2H-isothiazolin-3-one (MIT) (CAS NO 2682-20-4), octylisothiazolinone (OIT) (CAS NO 26530-20-1), dichlorooctylisothiazolinone (DOIT) (CAS NO 64359-81-5) and mixtures thereof. For example, the isothiazolinone biocide CMIT/MIT (CAS NO 55965-84-9) is a mixture of 5-chloro-2-methyl-2H-isothiazolin-3-one (CMIT) and 2-methyl-2H-isothiazolin-3-one (MIT) at a weight ratio of 3:1.

The aldehyde-containing compound is preferably selected from the group comprising formaldehyde (CAS NO 50-00-0), acetaldehyde, glyoxal, glutaraldehyde (CAS NO 111-30-8), 2-propenal, phthalic dialdehyde and mixtures thereof, and preferably is formaldehyde, glutaraldehyde or mixtures thereof.

In accordance with the present invention, an "aldehyde-containing biocide" refers to a biocide which has one or more aldehyde-group.

The aldehyde-releasing biocide is preferably selected from the group comprising formaldehyde-releasing biocides, acetaldehyde-releasing biocides, succinaldehyde-releasing biocides, 2-propenal-releasing biocides and mixtures thereof, preferably from formaldehyde-releasing biocides. The formaldehyde-releasing biocide is preferably selected from the group comprising benzyl alcoholmono(poly)-hemiformal (CAS NO 14548-60-8), tetramethylolacetylenediurea (CAS NO 5395-50-6), thiadiazinethione-tetrahydrodimethyl (DAZOMET) (CAS NO 533-74-4), (ethylenedioxy)dimethanol (EDDM) (CAS NO 3586-55-8), 2-chloro-N-(hydroxymethyl)acetamide (CAS NO 2832-19-1), dimethyloxazolidine (DMO) (CAS NO 51200-87-4), hexamethylenetetramine (CAS NO 100-97-0), bis[tetrakis(hydroxymethyl)phosphonium] sulphate (THPS) (CAS NO 55566-30-8), 1-(cis-3-chloroallyl)-3,5,7-triaza-1-azoniaadamantane chloride (CAS NO 51229-78-8), hexahydro-1,3,5-tris(hydroxyethyl)-s-triazine (CAS NO 4719-04-4) and mixtures thereof.

In accordance with the present invention, an "aldehyde-releasing biocide" refers to a compound which is able to release mono- di-, and/or tri-aldehyde.

The guanidine biocide is preferably selected from guanidinedodecyl monochloride (CAS NO 13590-97-1) and/or polyethoxyethoxyethylguanidinium hexachloride (CAS NO 374572-91-5). The sulphone biocide is preferably hexachlorodimethyl sulfone (CAS NO 3064-70-8) and/or 4,4'-Diaminodiphenylsulfone (CAS NO 80-08-0). The thiocyanate biocide is preferably methylene bis(thiocyanate) (CAS NO 6317-18-6) and/or (Benzothiazol-2-ylthio)methylthiocyanate (CAS NO 21564-17-0). The biocide being an antibiotic is preferably selected from β-lactam antibiotics such as penicillin G (CAS NO 69-57-8) and/or ampicillin (CAS NO 69-53-4) and/or biapenem (CAS NO 120410-24-4) and/or cefixime (CAS NO 79350-37-1). The amide biocide is preferably 2,2-dibromo-3-nitrilopropionamide (DBNPA) (CAS NO 10222-01-2). The azole biocide can be preferably selected from climbazole (CAS NO 38083-17-9), miconazole (CAS NO 22916-47-8), clotrimazole (CAS NO 23593-75-1), and mixtures thereof including the biocides in the form of a salt such as miconazole nitrate (CAS NO 22832-87-7). The carbamate biocide can be preferably selected from iodopropynyl butylcarbamate (CAS NO 55406-53-6), aldicarb (CAS NO 116-06-3), carbofuran (CAS NO 1563-66-2) and mixtures thereof. The glyphosate biocide is preferably selected from N-(phosphonomethyl)glycin (CAS NO 1071-83-6) and/or N-(phosphonomethyl)glycin in the form of the salt such as the ammonium salt or isopropylammonium salt (CAS NO 40465-66-5 and CAS NO 38641-94-0).

The pyrithione biocide is preferably sodium pyrithione (CAS NO 3811-73-2) and/or zinc pyrithione (CAS NO 13463-41-7).

The further biocide can be also preferably selected from quaternary ammonium salts, peroxides, perchlorates, tributyl tin, heavy metals, biocidal enzymes, biocidal polypeptides, sulphonamides and mixtures thereof.

In one embodiment of the present invention, the instant process further comprises step f) of dry grinding the mixture of the at least one inorganic filler material of step a), the one or more source of lithium ions of step b) and the one or more source of sodium ions of step c) obtained during and/or after process step d) and e).

For example, the instant process further comprises step f) of dry grinding the mixture of the at least one inorganic filler material of step a), the one or more source of lithium ions of step b) and the one or more source of sodium ions of step c) obtained during and after process step d) and e). Alternatively, the instant process further comprises step f) of dry grinding the mixture of the at least one inorganic filler material of step a), the one or more source of lithium ions of step b) and the one or more source of sodium ions of step c) obtained during or after process step d) and e). Preferably, the instant process further comprises step f) of dry grinding the mixture of the at least one inorganic filler material of step a), the one or more source of lithium ions of step b) and the one or more source of sodium ions of step c) obtained after process step d) and e).

The term "dry ground" or "dry grinding" in the meaning of the present invention refers to the comminution of a solid material by using a mill (e.g., by means of a ball mill, pin mill, rod mill and/or jet plate mill), wherein the material to be ground has a total moisture content of <15.0 wt.-%, preferably ≤5.0 wt.-% based on the total weight of said material.

For the purposes of the present invention, any suitable mill known in the art may be used. However, said at least one grinding unit preferably is a ball mill. It is appreciated that dry grinding is carried out by using at least one grinding unit, preferably one grinding unit, i.e. it is also possible to use a series of grinding units which may, for example, be selected from ball mills, semi-autogenous mills, pin mills or autogenous mills.

The amount of water being present in the mixture of the at least one inorganic filler material, the one or more source of lithium ions and the one or more source of sodium ions to be ground may be expressed by the total moisture content which is based on the total weight of said mixture. Typically, dry grinding processes are carried out using mixtures having a total moisture of <15.0 wt.-%, based on the total weight of said mixture.

According to one embodiment, the total moisture content in said mixture during dry grinding is ≤5.0 wt.-%, preferably ≤1.0 wt.-% and more preferably ≤0.2 wt.-% based on the total weight of said mixture.

According to another embodiment, the total moisture content in said mixture during dry grinding is ≤5.0 wt.-%, preferably ≤1.0 wt.-%, more preferably ≤0.2 wt.-%, and most preferably ≤0.15 wt.-%, based on the total weight of said mixture, wherein the total moisture content in the mixture during dry grinding preferably has a lower limit of 0.03 wt.-%, based on the total weight of said mixture.

Dry grinding can be carried out in a broad temperature range. For the purposes of the present invention, a temperature ranging from 20° C. to 200° C. is suitable, more preferably from 20° C. to 150° C. and most preferably from 20° C. to 80° C. can be used during dry grinding.

Dry grinding of the mixture of the at least one inorganic filler material, the one or more source of lithium ions and the one or more source of sodium ions is carried out in at least one grinding unit to obtain a dry ground material.

In one embodiment, the dry ground material obtained after dry grinding step f) has a volume median particle $d_{50}$ ranging from 0.1 to 10.0 μm, preferably from 0.2 to 5.0 μm, more preferably from 0.3 to 3.0 μm and most preferably from 0.5 to 3.0 μm, measured according to the dry laser diffraction method, preferably by using Mastersizer 3000 including an Aero S dry powder disperser from Malvern Instruments Ltd., United Kingdom.

Additionally or alternatively, the dry ground material obtained after dry grinding step f) has a particle size distribution such that from 80.0 vol.-% to 95.0 vol.-% of the particles will have an esd generally of less than 11.0 μm, 50.0 to 90.0 vol.-% less than 5.0 μm and 40.0 to 90.0 vol.-% less than 3.0 μm, measured according to the dry laser diffraction method, preferably by using Mastersizer 3000 including an Aero S dry powder disperser from Malvern Instruments Ltd., United Kingdom. In one embodiment, 80.0 to 90.0 vol.-% of the particles of the dry ground material obtained after dry grinding step f) have a particle esd of less than 11.0 μm, 50.0 to 70.0 vol.-% less than 5.0 μm and 40.0 to 50.0 vol.-% of less than 3.0 μm, measured according to the dry laser diffraction method, preferably by using Mastersizer 3000 including an Aero S dry powder disperser from Malvern Instruments Ltd., United Kingdom.

Additionally or alternatively, the instant process further comprises step f) of contacting the mixture of the at least one inorganic filler material, the one or more source of lithium ions and the one or more source of sodium ions obtained after step d) and e) with water and/or at least one dispersing agent.

A suitable dispersing agent according to the present invention is for example a salt of poly(acrylic acid) and/or poly (methacrylic acid).

Additionally or alternatively, the mixture of the at least one inorganic filler material, the one or more source of lithium ions and the one or more source of sodium ions obtained after step d) and e) may be also contacted with water in order to obtain an aqueous suspension comprising the inorganic filler material.

It is appreciated that the solids content of the obtained aqueous suspension can be up to 85.0 wt.-%. For example, the solids content of the aqueous suspension is from 10.0 to 82.0 wt.-%, and more preferably from 20.0 to 80.0 wt.-%, based on the total weight of the aqueous suspension.

If the mixture of the at least one inorganic filler material, the one or more source of lithium ions and the one or more source of sodium ions obtained after step d) and e) is contacted with water, said contacting can be carried out by methods known in the art, by for example, dispersing, suspending or slurring the water-insoluble solids, preferably the at least one inorganic filler material with, if appropriate, addition of at least one dispersing agent and, if appropriate, further additives in water.

It is appreciated that the aqueous suspension obtained by contacting the mixture of the at least one inorganic filler material, the one or more source of lithium ions and the one or more source of sodium ions obtained after step d) and e) with water may be further contacted with additives typically found in aqueous inorganic filler material comprising preparations such as paint or coating formulations, slurries, cosmetic formulations, creams, gels, fungicidal wall plaster formulations and the like.

Alternatively, the instant process further comprises step f) of contacting the mixture of the at least one inorganic filler material, the one or more source of lithium ions and the one or more source of sodium ions obtained after step d) and e), or optionally the mixture obtained after dry grinding said mixture, with an organic polymer composition comprising at least one organic polymer resin being selected from the group consisting of a thermoplast, duroplast, elastomer and mixtures thereof and subjecting the obtained composition to conditions under which it is converted into an antiseptic polymer product.

The term "organic" polymer resin in the meaning of the present invention refers to a polymer resin comprising carbon.

The at least one organic polymer resin being selected from the group consisting of a thermoplast, duroplast, elastomer and mixtures thereof is preferably selected from the group comprising halogenated polymer resins, styrenic resins, acrylic resins, polyolefines, polycarbonate resins, polyester resins such as unsaturated polyester resins, polyurethane resins, polyamide resins, biopolymers, copolymers, polyvinyl chlorides, polylactides, acrylonitrile butadiene styrenes, synthetic rubbers, natural rubbers and mixtures thereof. For example, the at least one organic polymer resin being selected from the group consisting of a thermoplast, duroplast, elastomer and mixtures thereof is preferably a polyethylene (PE), polypropylene (PP), polyvinyl chloride (PVC), polyester such as polyethylene terephthalate (PET), natural rubber, synthetic rubber and mixtures thereof.

The mixture of the at least one dry inorganic filler material, the one or more source of lithium ions and the one or more source of sodium ions obtained after step d) and e), or optionally the mixture obtained after dry grinding said mixture, and the organic polymer composition comprising at least one organic polymer resin being selected from the group consisting of a thermoplast, duroplast, elastomer and mixtures thereof can be contacted by any conventional means known to the skilled person.

The step of contacting the mixture of the at least one inorganic filler material, the one or more source of lithium ions and the one or more source of sodium ions obtained after step d) and e) with the organic polymer composition comprising at least one organic polymer resin being selected from the group consisting of a thermoplast, duroplast, elastomer and mixtures thereof, preferably takes place under mixing conditions. The skilled man will adapt these mixing conditions and configurations of mixing devices, such as Banburry mixers, twin-screw mixers, co-kneaders or any other devices suitable for this operation, according to his needs. However, the listed devices are not to be considered to be of limiting character.

The obtained composition can be converted into an antiseptic polymer product by any process suitable for preparing a polymer product known to the skilled person.

It is appreciated that the organic polymer composition comprising at least one organic polymer resin being selected from the group consisting of a thermoplast, duroplast, elastomer and mixtures thereof may further comprise additives typically found in such compositions or the corresponding polymer products to be prepared such as films, plasters, diapers, tissues, paints, coatings, plastic products or adsorbing agents for aqueous and/or organic fluids.

In the art, many processes for the preparation of such polymer products are known. These processes include, without being limited to, extrusion processes, co-extrusion processes, extrusion coating processes, injection molding processes, blow molding processes, mixing processes, calendering processes, twin screw extrusion processes and thermoforming processes.

Antiseptic Product

Another object of the present invention resides in an antiseptic product having antimicrobial activity obtainable by the process of the present invention.

According to the present invention, it is especially preferred that the antiseptic product has antimicrobial activity against at least one strain of bacteria and/or at least one strain of mould and/or at least one strain of yeast. This either prevents the growth or accumulation of the at least one strain of bacteria and/or at least one strain of yeast and/or at least one strain of mould or leads to a reduction of the cfu value (colony forming unit) in or on the antiseptic product.

In one embodiment of the present invention, the at least one strain of bacteria is selected from the group consisting of gram-negative bacteria, gram-positive bacteria and mixtures thereof.

It is appreciated that gram-positive and gram-negative bacteria are well known in the art and are e.g. described in Biology of Microorganisms, "Brock", Madigan M T, Martinko J M, Parker J, 1997, $8^{th}$ Edition. In particular, such bacteria represent evolutionary very distantly related classes of bacteria each comprising of many bacterial families. Gram negative bacteria are characterized by two membranes (outer and inner membrane) while gram positive bacteria contain only one membrane. Usually, the former contains a high amount of lipopolysaccharide and a thin single-layer of peptidoglycan, while the latter has virtually no lipopolysaccharide, a multi-layered thick peptidocglycan and the coat contains teichoic acids. For these differences the Gram positive and Gram negative bacteria react differently on environmental influences. Methods for discriminating gram-positive and gram-negative bacteria include species identification by DNA sequencing techniques or biochemical characterizations. Alternatively, the number of membranes can be determined directly by thin section transmission electron microscopy.

The term "at least one strain of bacteria" in the meaning of the present invention means that the strain of bacteria comprises, preferably consists of, one or more strains of bacteria.

In one embodiment of the present invention, the at least one strain of bacteria comprises, preferably consists of, one strain of bacteria. Alternatively, the at least one strain of bacteria comprises, preferably consists of, two or more strains of bacteria. For example, the at least one strains of bacteria comprises, preferably consists of, two or three strains of bacteria. Preferably, the at least one strain of bacteria comprises, preferably consists of, two or more strains of bacteria.

For example, the at least one strain of bacteria is selected from the group comprising, preferably consisting of, *Escherichia* sp., *Staphylococcus* sp., *Thermus* sp., *Propionibacterium* sp., *Rhodococcus* sp., *Panninobacter* sp., *Caulobacter* sp., *Brevundimonas* sp., *Asticcacaulis* sp., *Sphingomonas* sp., *Rhizobium* sp., *Ensifer* sp., *Bradyrhizobium* sp., *Tepidimonas* sp., *Tepidicella* sp., *Aquabacterium* sp., *Pelomonas* sp., *Alcaligenis* sp., *Achromobacter* sp., *Ralstonia* sp., *Limnobacter* sp., *Massilia* sp., *Hydrogenophaga* sp., *Acidovorax* sp., *Curvibacter* sp., *Delftia* sp., *Rhodoferax* sp., *Alishewanella* sp., *Stenotrophomonas* sp., *Dokdonella* sp., *Methylosinus* sp., *Hyphomicrobium* sp., *Methylosulfomonas* sp., *Methylobacteria* sp., *Pseudomonas* sp., *Enterococcus* sp., *Myroides* sp., *Burkholderia* sp., *Alcaligenes* sp. and mixtures thereof.

Preferably, the at least one strain of bacteria is selected from the group comprising, preferably consisting of, *Escherichia* sp. such as *Escherichia coli*, *Staphylococcus* sp. such as *Staphylococcus aureus*, *Pseudomonas* sp. such as *Pseudomonas putida, Pseudomonas mendocina, Pseudomonas oleovorans, Pseudomonas fluorescens, Pseudomonas alcaligenes, Pseudomonas aeruginosa, Pseudomonas orizyhabitans, Pseudomonas pseudoalcaligenes, Pseudomonas entomophila, Pseudomonas syringae, Methylobacteria* sp. such as *Methylobacterium extorquens, Methylobacterium radiotolerants, Methylobacterium dichloromethanicum, Methylobacterium organophilu, Hyphomicrobium* sp. such as *Hyphomicrobium zavarzini, Enterococcus faecalis, Myroides odoratus, Burkholderia cepacia, Alcaligenes faecalis* and *Sphingomonas paucimobilis* and mixtures thereof.

Additionally or alternatively, the at least one strain of yeast is selected from the group comprising *Saccharomycotina, Taphrinomycotina, Schizosaccharomycetes, Basidiomycota, Agaricomycotina, Tremellomycetes, Pucciniomycotina, Microbotryomycetes, Candida* sp. such as *Candida albicans, Candida tropicalis, Candida stellatoidea, Candida glabrata, Candida krusei, Candida guilliermondii, Candida viswanathii, Candida lusitaniae* and mixtures thereof, *Yarrowia* sp. such as *Yarrowia lipolytica, Cryptococcus* sp. such as *Cryptococcus gattii* and *Cryptococcus neofarmans, Zygosaccharomyces* sp., *Rhodotorula* sp. such as *Rhodotorula mucilaginosa*, and mixtures thereof.

The term "at least one strain of yeast" in the meaning of the present invention means that the strain of yeast comprises, preferably consists of, one or more strains of yeast.

In one embodiment of the present invention, the at least one strain of yeast comprises, preferably consists of, one strain of yeast. Alternatively, the at least one strain of yeast comprises, preferably consists of, two or more strains of yeast. For example, the at least one strains of yeast comprises, preferably consists of, two or three strains of yeast. Preferably, the at least one strain of yeast comprises, preferably consists of, two or more strains of yeast.

Additionally or alternatively, the at least one strain of mould is selected from the group comprising of *Acremonium* sp., *Alternaria* sp., *Aspergillus* sp., *Cladosporium* sp., *Fusarium* sp., *Mucor* sp., *Penicillium* sp., *Rhizopus* sp., *Stachybotrys* sp., *Trichoderma* sp., *Dematiaceae* sp., *Phoma* sp., *Eurotium* sp., *Scopulariopsis* sp., *Aureobasidium* sp., *Monilia* sp., *Botrytis* sp., *Stemphylium* sp., *Chaetomium* sp., *Mycelia* sp., *Neurospora* sp., *Ulocladium* sp., *Paecilomyces* sp., *Wallemia* sp., *Curvularia* sp., and mixtures thereof.

The term "at least one strain of mould" in the meaning of the present invention means that the strain of mould comprises, preferably consists of, one or more strains of mould.

In one embodiment of the present invention, the at least one strain of mould comprises, preferably consists of, one strain of mould. Alternatively, the at least one strain of mould comprises, preferably consists of, two or more strains of mould. For example, the at least one strains of mould comprises, preferably consists of, two or three strains of mould. Preferably, the at least one strain of mould comprises, preferably consists of, two or more strains of mould.

It is preferred that the antiseptic product has antimicrobial activity against at least one strain of bacteria and at least one strain of yeast and at least one strain of mould when present in or on the inorganic filler material comprising product.

Alternatively, the antiseptic product has antimicrobial activity against at least one strain of bacteria or at least one strain of yeast or at least one strain of mould when present in or on the inorganic filler material comprising product.

Alternatively, the antiseptic product has antimicrobial activity against at least one strain of bacteria and at least one strain of yeast or at least one strain of mould when present in or on the antiseptic product or the antiseptic product has antimicrobial activity against at least one strain of bacteria or at least one strain of yeast and at least one strain of mould when present in or on the antiseptic product.

Preferably, the antiseptic product has antimicrobial activity against at least one strain of bacteria or at least one strain of yeast or at least one strain of mould when present in or on the antiseptic product. More preferably, the antiseptic product has antimicrobial activity against at least one strain of bacteria or at least one strain of yeast when present in or on the antiseptic product. Most preferably, the antiseptic product has antimicrobial activity against at least one strain of bacteria when present in or on the antiseptic product.

It is appreciated that the antiseptic product having antimicrobial activity comprises the one or more source of lithium ions in an amount such that the total amount of lithium ions in the final antiseptic product is from 20 to 60 000 ppm, preferably from 20 to 30 000 ppm and most preferably from 20 to 10 000 ppm, based on the total weight of the antiseptic product, and the one or more source of sodium ions in an amount such that the total amount of sodium ions in the final antiseptic product is from 20 to 20 000 ppm, preferably from 20 to 10 000 ppm and most preferably from 20 to 5 000 ppm, based on the total weight of the antiseptic product.

Preferably, the antimicrobial activity means that the antiseptic product maintains a cfu/ml value of less than $10^4$ cfu/ml, more preferably of less than $10^3$ cfu/ml, and even more preferably of less than $10^2$ cfu/ml on contamination with the at least one strain of bacteria and/or at least one strain of mould and/or at least one strain of yeast.

Said final antiseptic product having antimicrobial activity obtainable by the process of the present invention may be a paint or coating formulation, non-aqueous slurry, cosmetic formulation, cream, gel, fungicidal wall plaster formulation, film, plaster, diaper, tissue, plastic product or adsorbing agent for aqueous and/or organic fluids such as human and/or animal liquids, e.g. urine, blood, serum, sweat, saliva, interstitial fluid, cerebrospinal fluid, milk, semen, vaginal fluid and the like, or organic liquids such as vegetable and fruit juice.

In view of the above, the antiseptic product can be an antiseptic inorganic powder composition and/or an antiseptic polymer product.

Thus, the present invention refers in a further aspect to an antiseptic inorganic powder composition.

The antiseptic inorganic powder composition comprises
 a) at least one inorganic filler material,
 b) 20 to 20 000 ppm of one or more source of sodium ions, based on the total weight of the antiseptic inorganic powder composition, and
 c) 20 to 60 000 ppm of one or more source of lithium ions, based on the total weight of the antiseptic inorganic powder composition,
  wherein the molar ratio of sodium ions:lithium ions (Na:Li) in the antiseptic inorganic powder composition is from 1:1 to 1:10 and the moisture content of the antiseptic inorganic powder composition is <15.0 wt.-%, based on the total weight of the antiseptic inorganic powder composition.

With regard to the definition of the at least one inorganic filler material, the one or more source of sodium ions, the one or more source of lithium ions and preferred embodiments thereof, reference is made to the statements provided above when discussing the technical details of the process of the present invention.

It is appreciated that the antiseptic inorganic powder composition comprises the one or more source of lithium ions in an amount such that the total amount of lithium ions in the final antiseptic product is from 20 to 60 000 ppm, preferably from 20 to 30 000 ppm and most preferably from 20 to 10 000 ppm, based on the total weight of the antiseptic inorganic powder composition, and the one or more source of sodium ions in an amount such that the total amount of sodium ions in the final antiseptic inorganic powder composition is from 20 to 20 000 ppm, preferably from 20 to 10 000 ppm and most preferably from 20 to 5 000 ppm, based on the total weight of the antiseptic inorganic powder composition.

It is one specific requirement of the instant antiseptic inorganic powder composition that the molar ratio of sodium ions:lithium ions (Na:Li) in the antiseptic inorganic powder composition is from 1:1 to 1:10. For example, the molar ratio of sodium ions:lithium ions (Na:Li) in the antiseptic inorganic powder composition is from 1:1.1 to 1:10, preferably from 1:1.5 to 1:10 and most preferably from 1:2 to 1:8.

It is further appreciated that the antiseptic inorganic powder composition has a moisture content of <15.0 wt.-%, based on the total weight of the antiseptic inorganic powder composition. For example, the moisture content of the antiseptic inorganic powder composition is ≤5.0 wt.-%, preferably ≤1.0 wt.-%, more preferably ≤0.2 wt.-%, and most preferably from 0.03 to 0.15 wt.-%, based on the total weight of the antiseptic inorganic powder composition.

In one embodiment, the at least one inorganic filler material in the antiseptic inorganic powder composition has a volume median diameter $d_{50}$ value from 0.5 to 25.0 µm, preferably from 0.7 to 5.0 µm, more preferably from 1.0 to 4.0 µm and most preferably from 1.5 to 3.5 µm, measured according to the dry laser diffraction method, preferably by using Mastersizer 3000 including an Aero S dry powder disperser from Malvern Instruments Ltd., United Kingdom.

Additionally or alternatively, the one or more source of sodium ions and/or lithium ions in the antiseptic inorganic powder composition are/is a corresponding carbonate salt(s). Preferably, the one or more source of sodium ions and lithium ions in the antiseptic inorganic powder composition are corresponding carbonate salts. Alternatively, the one or more source of sodium ions or lithium ions in the antiseptic inorganic powder composition is a corresponding carbonate salt. Most preferably, the one or more source of sodium ions and lithium ions in the antiseptic inorganic powder composition are corresponding carbonate salts.

In one embodiment of the present invention, the antiseptic inorganic powder composition has hydrophobic surface properties.

It is appreciated that "hydrophobic surface properties" of the antiseptic inorganic powder composition is evaluated by determining the minimum methanol to water ratio in a methanol-water mixture needed for the settling of a majority of said inorganic powder composition, where said inorganic powder composition is deposited on the surface of said methanol-water mixture by passage through a house hold tea sieve.

The antiseptic inorganic powder composition of the present invention has hydrophobic surface properties if the majority of said antiseptic inorganic powder composition does not settle using a volume based solution of water:methanol ratio of 10:1.

Another aspect of the present invention refers to an antiseptic polymer product.

The antiseptic polymer product comprises
- a) an organic polymer composition comprising at least one organic polymer resin being selected from the group consisting of a thermoplast, duroplast, elastomer and mixtures thereof,
- b) 20 to 20 000 ppm of one or more source of sodium ions, based on the total weight of the antiseptic polymer composition,
- c) 20 to 60 000 ppm of one or more source of lithium ions, based on the total weight of the antiseptic polymer composition, and
- d) optionally at least one inorganic filler material, wherein the molar ratio of sodium ions:lithium ions (Na:Li) in the antiseptic polymer product is from 1:1 to 1:10 and the moisture content of the antiseptic polymer product is ≤1.0 wt.-%, based on the total weight of the antiseptic polymer product.

In one embodiment, the antiseptic polymer product comprises, preferably consists of,
- a) an organic polymer composition comprising at least one organic polymer resin being selected from the group consisting of a thermoplast, duroplast, elastomer and mixtures thereof,
- b) 20 to 20 000 ppm of one or more source of sodium ions, based on the total weight of the antiseptic polymer composition, and
- c) 20 to 60 000 ppm of one or more source of lithium ions, based on the total weight of the antiseptic polymer composition, wherein the molar ratio of sodium ions:lithium ions (Na:Li) in the antiseptic polymer product is from 1:1 to 1:10 and the moisture content of the antiseptic polymer product is ≤1.0 wt.-%, based on the total weight of the antiseptic polymer product.

In another embodiment, the antiseptic polymer product comprises, preferably consists of,
- a) an organic polymer composition comprising at least one organic polymer resin being selected from the group consisting of a thermoplast, duroplast, elastomer and mixtures thereof,
- b) 20 to 20 000 ppm of one or more source of sodium ions, based on the total weight of the antiseptic polymer composition,
- c) 20 to 60 000 ppm of one or more source of lithium ions, based on the total weight of the antiseptic polymer composition, and
- d) at least one inorganic filler material, wherein the molar ratio of sodium ions:lithium ions (Na:Li) in the antiseptic polymer product is from 1:1 to 1:10 and the moisture content of the antiseptic polymer product is ≤1.0 wt.-%, based on the total weight of the antiseptic polymer product.

With regard to the definition of the organic polymer composition, the one or more source of sodium ions, the one or more source of lithium ions, the at least one inorganic filler material and preferred embodiments thereof, reference is made to the statements provided above when discussing the technical details of the process of the present invention.

The at least one organic polymer resin being selected from the group consisting of a thermoplast, duroplast, elastomer and mixtures thereof is preferably selected from the group comprising halogenated polymer resins, styrenic resins, acrylic resins, polyolefines, polycarbonate resins, polyester resins such as unsaturated polyester resins, polyurethane resins, polyamide resins, biopolymers, copolymers, polyvinyl chlorides, polylactides, acrylonitrile butadiene styrenes, synthetic rubbers, natural rubbers and mixtures thereof.

For example, the at least one organic polymer resin being selected from the group consisting of a thermoplast, duroplast, elastomer and mixtures thereof is preferably a polyethylene (PE), polypropylene (PP), polyvinyl chloride (PVC), polyester such as polyethylene terephthalate (PET), natural rubber, synthetic rubber and mixtures thereof.

It is appreciated that the antiseptic polymer product comprises the one or more source of lithium ions in an amount such that the total amount of lithium ions in the final antiseptic polymer product is from 20 to 60 000 ppm, preferably from 20 to 30 000 ppm and most preferably from 20 to 10 000 ppm, based on the total weight of the antiseptic polymer product, and the one or more source of sodium ions in an amount such that the total amount of sodium ions in the final antiseptic polymer product is from 20 to 20 000 ppm, preferably from 20 to 10 000 ppm and most preferably from 20 to 5 000 ppm, based on the total weight of the antiseptic polymer product.

It is one specific requirement of the instant antiseptic polymer product that the molar ratio of sodium ions:lithium ions (Na:Li) in the antiseptic polymer product is from 1:1 to 1:10. For example, the molar ratio of sodium ions:lithium ions (Na:Li) in the antiseptic polymer product is from 1:1.1 to 1:10, preferably from 1:1.5 to 1:10 and most preferably from 1:2 to 1:8.

It is further appreciated that the antiseptic polymer product has a moisture content of <1.0 wt.-%, based on the total weight of the antiseptic polymer product. For example, the moisture content of the antiseptic polymer product is ≤0.8 wt.-%, preferably ≤0.5 wt.-%, more preferably ≤0.2 wt.-%, and most preferably from 0.03 to 0.15 wt.-%, based on the total weight of the antiseptic polymer product.

In one embodiment, the at least one inorganic filler material in the antiseptic polymer product has a volume median diameter $d_{50}$ value from 0.5 to 25.0 µm, preferably from 0.7 to 5.0 µm, more preferably from 1.0 to 4.0 µm and most preferably from 1.5 to 3.5 µm, measured according to the dry laser diffraction method, preferably by using Mastersizer 3000 including an Aero S dry powder disperser from Malvern Instruments Ltd., United Kingdom.

Additionally or alternatively, the one or more source of sodium ions and/or lithium ions in the antiseptic polymer product are/is a corresponding carbonate salt(s). Preferably, the one or more source of sodium ions and lithium ions in the antiseptic polymer product are corresponding carbonate salts. Alternatively, the one or more source of sodium ions or lithium ions in the antiseptic polymer product is a corresponding carbonate salt. Most preferably, the one or more source of sodium ions and lithium ions in the antiseptic polymer product are corresponding carbonate salts.

If the antiseptic polymer product comprises at least one filler material, the at least one inorganic filler material is preferably the carrier for the sodium ion and/or lithium ion source. That is to say, the one or more source of sodium ions, the one or more source of lithium ions and the at least one inorganic filler material are preferably present in the antiseptic polymer product as a blend.

Use of One or More Source of Lithium Ions in Combination with One or More Source of Sodium Ions for the Preparation of an Antiseptic Product The present invention also refers to the use of one or more source of lithium ions in combination with one or more source of sodium ions for the preparation of an antiseptic product being effective against microbial contamination.

It is one requirement of the instant use that the one or more source of lithium ions is used in combination with the one or more source of sodium ions such that the final antiseptic product comprises the a) one or more source of lithium ions in an amount such that the total amount of lithium ions in the antiseptic product is from 20 to 60 000 ppm, based on the total weight of the antiseptic product, and b) one or more source of sodium ions in an amount such that the total amount of sodium ions in the antiseptic product is from 20 to 20 000 ppm, based on the total weight of the antiseptic product.

Preferably, the antiseptic product comprises the one or more source of lithium ions in an amount such that the total amount of lithium ions in the final antiseptic product is from 20 to 30 000 ppm and most preferably from 20 to 10 000 ppm, based on the total weight of the antiseptic product, and the one or more source of sodium ions in an amount such that the total amount of sodium ions in the final antiseptic product is from 20 to 10 000 ppm and most preferably from 20 to 5 000 ppm, based on the total weight of the antiseptic product.

In one embodiment, the one or more source of lithium ions and the one or more source of sodium ions are used in a blend.

In one embodiment of the present invention, no further biocide is employed in the antiseptic product in addition to the antiseptic effect formed by combining the one or more source of lithium ions with the one or more source of sodium ions.

With regard to the definition of the one or more source of lithium ions, the one or more source of sodium ions and the antiseptic product and preferred embodiments thereof, reference is made to the statements provided above when discussing the technical details of the process and the antiseptic product of the present invention.

The following examples may additionally illustrate the invention, but are not meant to restrict the invention to the exemplified embodiments. The examples below show the good antiseptic effect of the one or more source of lithium ions in combination with the one or more source of sodium ions when employed in an antiseptic product according to the invention.

EXAMPLES

Measurement Processes

The following measurement processes were used to evaluate the parameters given in the examples and claims.

BET Specific Surface Area of a Material

The BET specific surface area was measured via the BET process according to ISO 9277 using nitrogen.

Particle Size Distribution (Vol.-% Particles with a Esd (Equivalent Spherical Diameter) <X)

Median grain diameter and grain volume distribution of the particulate material were determined via the dry laser diffraction method using a Malvern Mastersizer 3000 (Malvern Instruments GmbH, Herrenberg, Germany) in combination with the Aero S dry powder disperser using compressed air of 1 bar to disperse the sample. Calculation was done with the Frauenhofer scattering model. The method is known to the skilled person.

pH Measurement

The pH of aqueous samples is measured by using a standard pH-meter at approximately 25° C.

Amounts of Sodium and Lithium

All sodium and lithium amounts quoted in ppm represent mg values per kilogram of the final product.

Hydrophobic Surface Properties

Hydrophobic surface properties of an inorganic powder material is evaluated by determining the minimum methanol to water ratio in a methanol-water mixture needed for the settling of a majority of said inorganic powder material, where said inorganic powder material is deposited on the surface of said methanol-water mixture by passage through a house hold tea sieve.

Preparation of Bacteria, Yeast and Mould Used

Fresh bacteria cultures of the bacteria *Enterococcus faecalis*, e.g. *E. faecalis* strain ATCC-11420, *Escherichia coli*, e.g. *E. coli* strains ATCC-11229 and DSM 1386, *Myroides odoratus*, e.g. *M. odoratus* ATCC-4651, *Pseudomonas* sp., e.g. *P. aeruginosa* ATCC-10145 and *P. orizyhabitans* ATCC-43272, *Burkholderia cepacia*, e.g. *B. cepacia* ATCC-21809, *Alcaligenes faecalis*, e.g. *A. faecalis* ATCC-25094, *Sphingomonas paucimobilis*, e.g. *S. paucimobilis* ATCC-BAA-1092 and *Staphylococcus aureus*, e.g. *S. aureus* strains DSM 346, were prepared by inoculation of 3 ml liquid growth media (tryptic soy broth, e.g. Fluka, No. 22092) from a single colony of a stock culture and incubation for 16 to 20 h at 30° C. with agitation at 150 rotations per minutes (rpm) leading to a cell density of approximately $2\times10^8$ cells/ml. Fresh cultures of the resistant bacteria rOmyAK adapted to the conditions in biocide containing $CaCO_3$ slurries, were prepared by plating 10 ul from a stock culture on tryptic soy agar plates and incubating for 48 h at 30° C. From this culture, one colony was then inoculated in 3 ml liquid growth media as above. rOmyAK, is a *Pseudomonas* sp. strain resistant to a biocide mixture of 750 ppm 1,6-Dihydroxy-2,5-dioxane (CAS NO. 3586-55-8) and 19 ppm CMIT/MIT (CAS NO. 55965-84-9).

A fresh yeast culture of *Candida albicans*, e.g. *C. albicans* strain DSM 1386 was prepared in the same way as for instance *S. aureus* from a single colony from a stock culture grown on sabouraud glucose+chloramphenicol agar plates (e.g. Merck No. 1460030020).

A fresh culture of *Aspergillus niger*, e.g. *Aspergillus niger* DSM 1957 was prepared by inoculating a malt agar plate (1.5% agar e.g. Fluka, No. 5039 and 3% malt e.g. Fluka, No. 70167) with a stock culture by placing a piece of mycelium in the middle of the plate and incubating for 2 weeks at 25° C.

Antimicrobial Activity Tests of Dry Powder

Dry powders of $CaCO_3$, $Li_2CO_3$ and/or $Na_2CO_3$ were mixed in 12-well culture plates (e.g. TPP, NO. 92012) at different ratios as stated in the examples below. A total of 2 g of powder-mixture were filled in each well. Over-night cultures of bacteria and yeast (in tryptic soy broth) were diluted with water (to 10 ml water, 1 ml of culture was added). When a bacterial mix was prepared as inoculum, 1 ml of each bacteria over-night culture was mixed together and then this mixture was diluted as described above. Of this dilution, 800 ul was added to the prepared 2 g of powder and mixed well. The plates were then placed in a humid chamber to have a humidity of >90% during incubation and prevent drying. The plates were incubated at 30° C. for 24 h before plating and counting cfu as described below.

Bacteria and Yeast Counts of Antimicrobial Activity Tests of Dry Powder

When not otherwise indicated, the quoted bacterial and yeast counts are as cfu/plate. In the Tables here below they were determined after 2 days following plate-out and incubation at 30° C. The counting method was as follows. The aqueous preparations of dry powder mixed with the bacterial inoculum were stirred well with a cotton swab (e.g. Applimed SA, No. 1102245); leaving approximately 200 mg of aqueous preparation on the swab. Then three even streaks were made on a tryptic soy agar plate (TSA, prepared using BD 236950) from right to left and three more from top to bottom. TSA plates were then incubated for 48 h at 30° C. Colony forming units (cfu) were then counted and reported as cfu/plate.

Counts from 100 to 999 cfu per plate are reported as 100 cfu/plate, counts of 1 000 and more cfu with single colonies well distinguishable are reported as 1 000 cfu/plate, counts of 1 000 and more cfu with single colonies not well distinguishable anymore are reported as 10 000 cfu/plate and when only one even streak of bacteria was visible it is reported as 100 000 cfu/plate. For tests using bacteria mixtures, all counts equal or above 1 000 cfu/plate were reported as 1 000 cfu/plate, including 10'000 cfu/plate and 100 000 cfu/plate.

Antimicrobial Surface Activity Test of Plastic

To test the antimicrobial surface activity of plastic the Japanese Standard Protocol JIS Z 2801 2000 was followed using bacteria and yeast prepared as described above and diluted to an optical density at 600 nm of 0.1-0.09. The plating, counting and evaluation were done according to the Japanese Standard Protocol JIS Z 2801 2000.

In accordance with the Japanese Standard Protocol, the bacterial and yeast counts as cfu/test item and the antimicrobial activity of the specimen compared to control are reported.

Antimicrobial Surface Activity Test of Paint Against Mould

To test the antimicrobial surface activity of paints against moulds, the norm DIN E 15457:2007-10 was followed using the mould strain *Aspergillus niger* DSM 1957. To prepare the test items, the biocide-free paint, either containing lithium or sodium or as control a paint without lithium and sodium, was spread on a filter paper and air dried. In addition, slurry free of biocide and lithium and sodium was spread on a filter and air dried. The following deviations were made from the protocol: instead of three, one test item was prepared per treatment and the test items were not sterilized before the test. Instead, sterility of the reagents (i.e. paint and slurry) was confirmed prior to the test. In accordance with the norm, the results are given as degree of fungal growth on the test specimen at different days after inoculation. The rating for the degree of fungal growth is 0: No mycelium on the surface, 1: <10% growth on the surface, 2: 10%-30% growth on the surface, 3: 30%-50% growth on the surface, 4: 50%-100% growth on the surface.

Solids and Moisture Content

The solids and moisture content is measured using a Moisture Analyzer of Mettler-Toledo MJ33. The weight loss of the product is measured during drying at 150° C. The method and the instrument are known to the skilled person.

Test 1: Preparation of Dry Carbonate Powder $CaCO_3$, $Li_2CO_3$ and $Na_2CO_3$ were grinded in a 5 litre laboratory porcelain grinder to the desired size. From these powders, mixtures of 90 wt.-% $CaCO_3$ and 10 wt.-% $Li_2CO_3$ or 10 wt.-% $Na_2CO_3$, based on the total weight of the mixture, were prepared.

The $CaCO_3$ powder has the following properties: 90 vol.-% has an esd (equivalent spherical diameter) of <10.3 µm ($d_{90}$), 50 vol.-% of <3.19 µm ($d_{50}$) and 10 vol.-% of <0.461 µm ($d_{10}$).

The $Li_2CO_3$ powder has the following properties: 90 vol.-% has an esd of <50.6 µm ($d_{90}$), 50 vol.-% of <3.86 µm ($d_{50}$) and 10 vol.-% of <0.498 µm ($d_{10}$).

The $Na_2CO_3$ powder has the following properties: 90 vol.-% has an esd of <27.6 µm ($d_{90}$), 50 vol.-% of <2.31 µm ($d_{50}$) and 10 vol.-% of <0.659 µm ($d_{10}$).

The mixture of $CaCO_3$ and $Li_2CO_3$ has the following properties: 90 vol.-% has an esd of <11.5 µm ($d_{90}$), 50 vol.-% of <3.25 µm ($d_{50}$) and 10 vol.-% of <0.481 µm ($d_{10}$).

The mixture of $CaCO_3$ and $Na_2CO_3$ has the following properties: 90 vol.-% has an esd of <11.6 µm ($d_{90}$), 50 vol.-% of <3.15 µm ($d_{50}$) and 10 vol.-% of <0.453 µm ($d_{10}$).

Test 2: Preparation of the Polymer Product Containing Lithium and Sodium Carbonate The polymer product was prepared using a Collins automatic roller mill (150 mm radius; 400 mm length) by adding first 90 g of polyethylene (Exon Mobil LLDPE Linear Low Density Polyethylene) and after complete melting 10 g of dry powder with different amounts of $CaCO_3$, $Li_2CO_3$ and $Na_2CO_3$ as specified below in the examples. The mixture was homogenized removing the plastic and placing it back into the machine 5 times. The resulting polymer had a thickness of 0.7 mm.

Test 3: Preparation of the Paint Containing Lithium and Sodium Carbonate

The paint was produced using slurry containing 500 ppm lithium ions (from $Li_2CO_3$) and 1000 ppm sodium ions (from $Na_2CO_3$), based on the total weight of solid content in the slurry.

The paint was a high gloss emulsion paint consisting of 0.3 wt.-% Tafigel PUR 41, 0.3 wt.-% Tego Foamex 810, 1.6 wt.-% Tego Dispers 750, 0.9 wt.-% Texanol, 0.6 wt.-% Dowanol DPnB, 20.3 wt.-% Titandioxide TiONA 595, 4.9 wt.-% $CaCO_3$ slurry (solid content: 78.8 wt.-% containing 500 ppm lithium per dry, 1000 ppm sodium per dry), 0.8 wt.-% Tafigel PUR 45, Texanol, 1 wt.-% propyleneglycole, 0.8 wt.-% Byk 381 (Fk: 52%), 0.2 wt.-% Byk 349 (Fk: 100%), 0.2 wt.-% Tego Glide 450 (Fk. 100%), 1.5 wt.-% Methoxybutanol, 56 wt.-% Mowilith LDM 7717 (46%) and 3 wt.-% Südranol 240 and water to 100 wt.-%, based on the total weight of the paint. This resulted finally in a lithium content of 20 ppm and a sodium content of 40 ppm in the final product. The final solids content was 53.68 wt.-%, based on the total weight of the paint.

For the testing, the paint was spread on filter paper (Whatman GF/D 42.5 mm, VWR 513-5254) and air-dried before the antimicrobial test was performed.

Example 1: Antimicrobial Activity of Dry Powder Containing Lithium and Sodium Ions Against Single Strains of Bacteria The antimicrobial activity of dry calcium carbonate powder (moisture content <0.2 wt.-%, based on the total weight of the powder) containing lithium and/or sodium ions when in contact with water is shown in Table 1 below. The bacterial strains *S. aureus, E. faecalis* and rOmyAK were added to dry powder containing differing amounts of lithium and sodium, alone or in combination. The results show a synergistic effect of lithium and sodium carbonate when added together, compared to their single activity. Thus, the bacterial burden can be reduced up to 10 000-fold when both lithium and sodium carbonate are added in combination (synergistic effect), compared to samples with only one ion source. The control was done using plain $CaCO_3$ powder and always showed a bacterial burden above $1 \times 10^5$ cfu/plate.

TABLE 1

Reduction of bacterial counts in an aqueous preparation upon addition to dry powder containing lithium and/or sodium ions. Dry CaCO₃ powder containing different amounts of lithium and/or sodium ions

| | | | | | | |
|---|---|---|---|---|---|---|
| Sodium ions | (ppm w/w) | 0 | 0 | 230 | 230 | Synergistic reduction |
| Lithium ions | (ppm w/w) | 0 | 105 | 0 | 105 | |
| Enterococcus faecalis ATCC-11420 | (cfu/plate) | $10^5$ | $10^5$ | $10^5$ | $10^4$ | 10-fold |
| Staphylococcus aureus DSM 346 | (cfu/plate) | $10^5$ | $10^5$ | $10^5$ | $10^3$ | 100-fold |
| Pseudomonas mendocina - rOmyAK | (cfu/plate) | $10^5$ | $10^4$ | $10^5$ | 0 | 10'000-fold |

From table 1 it can be gathered that all three bacteria species tested were susceptible to a combination of lithium and sodium ions. The synergistic effect reduced bacterial counts up to 10 000-fold.

Example 2: Antimicrobial Activity of Dry Powder Containing High Amounts of Lithium and Sodium Ions Against Complex Mixtures of Bacteria The antimicrobial activity of dry calcium carbonate powder (moisture content <0.2 wt.-%, based on the total weight of the powder) containing lithium and/or sodium ions when in contact with water and a mixture of bacteria is shown in Table 2 below. The bacteria *E. faecalis* strain ATCC-11420, *E. coli* strain ATCC-11229, *M. odoratus* ATCC-4651, *P. aeruginosa* ATCC-10145, *P. orizyhabitans* ATCC-43272, *B. cepacia* ATCC-21809, *A. faecalis* ATCC-25094 and *S. paucimobilis* ATCC-BAA-1092 were added to dry powder containing differing amounts of lithium and sodium, alone or in combination. The results show a synergistic effect of the two ions when added together, compared to their single activity. The negative control was done using plain CaCO₃ powder, i.e. without addition of lithium or sodium carbonate and showed always a bacterial load of 1×10⁴ cfu/plate.

TABLE 2

A&B: Reduction of bacterial counts in an aqueous preparation upon addition to dry powder containing lithium and/or sodium ions.

A

CaCO3 powder containing different amounts of lithium and/or sodium ions added as carbonate salt

| | | | | | | |
|---|---|---|---|---|---|---|
| Sodium ions | (ppm w/w) | 0 | 5000 | 0 | 5000 | Synergistic reduction |
| Lithium ions | (ppm w/w) | 0 | 0 | 15000 | 15000 | |
| Mixture of 8 Strains[1] | (cfu/plate) | $10^4$ | $10^4$ | 72 | 0 | >72-fold |

B

CaCO3 powder containing different amounts of lithium and/or sodium ions added as carbonate salt

| | | | | | | |
|---|---|---|---|---|---|---|
| Sodium ions | (ppm w/w) | 0 | 20000 | 0 | 20000 | Synergistic reduction |
| Lithium ions | (ppm w/w) | 0 | 0 | 57000 | 57000 | |

TABLE 2-continued

A&B: Reduction of bacterial counts in an aqueous preparation upon addition to dry powder containing lithium and/or sodium ions.

| | | | | | | |
|---|---|---|---|---|---|---|
| Mixture of 8 Strains[1] | (cfu/plate) | $10^4$ | $10^4$ | 56 | 0 | >56-fold |

[1]*Myroides odoratus* ATCC-4651, *Pseudomonas aeruginosa* ATCC-10145, *Pseudomonas orizyhabitans* ATCC-43272, *Burkholderia cepacia* ATCC-21809, *E. coli* ATCC-11229, *Alcaligenes faecalis* ATCC-25094, *Sphingomonas paucimobilis* ATCC-BAA-1092, *Enterococcus faecalis* strain ATCC-11420

From tables 2A and 2B, it can be gathered that the bacterial mixture was much more susceptible to a combination of lithium and sodium ions. The synergistic effect reduced bacterial counts at least 72-fold.

Example 3: Antimicrobial Activity of Dry Powder Containing Different Lithium and Sodium Ion Sources Against Single Strains of Bacteria The antimicrobial activity of dry calcium carbonate powder (moisture content <0.2 wt.-%, based on the total weight of the powder) containing lithium and/or sodium ions from either carbonate salts (moisture content <0.2 wt.-%, based on the total weight of the carbonate salt) or chloride salts (moisture content <0.2 wt.-%, based on the total weight of the chloride salt) when in contact with water and bacteria, is shown in Table 3 below. The bacteria *E. faecalis* strain ATCC-11420 and *S. aureus* DSM 346 were added to dry calcium carbonate powder containing differing amounts of lithium ions and sodium ions, alone or in combination derived either from its carbonate or chloride salt. The results show a synergistic effect of the two ions when added together, compared to their single activity despite the anion. Both the addition of the lithium ions and sodium ions as carbonate salt or chloride salt show this synergistic effect. The negative control was done using plain CaCO₃ powder, i.e. without addition of lithium carbonate or sodium carbonate and showed always a bacterial load of 1×10³ cfu/plate.

TABLE 3

A&B: Reduction of bacterial counts in an aqueous preparation upon addition to dry powder containing lithium and/or sodium ions from different sources.

A

CaCO3 powder containing different amounts of lithium and/or sodium ions added as carbonate salt

| | | | | | | |
|---|---|---|---|---|---|---|
| Sodium ions | (ppm w/w) | 0 | 10000 | 0 | 10000 | Synergistic reduction |
| Lithium ions | (ppm w/w) | 0 | 0 | 15000 | 15000 | |
| Enterococcus faecalis ATCC-11420 | (cfu/plate) | $10^3$ | 83 | 26 | 1 | >20-fold |
| Staphylococcus aureus DSM 346 | (cfu/plate) | $10^3$ | 0 | 0 | 1 | n.a. |

B

CaCO3 powder containing different amounts of lithium and/or sodium ions added as chloride salt

| | | | | | | |
|---|---|---|---|---|---|---|
| Sodium ions | (ppm w/w) | 0 | 10000 | 0 | 10000 | Synergistic reduction |
| Lithium ions | (ppm w/w) | 0 | 0 | 15000 | 15000 | |

TABLE 3-continued

A&B: Reduction of bacterial counts in an aqueous preparation upon addition to dry powder containing lithium and/or sodium ions from different sources.

| Enterococcus faecalis ATCC-11420 | (cfu/plate) | $10^3$ | $10^3$ | $10^2$ | 0 | >100-fold |
|---|---|---|---|---|---|---|
| Staphylococcus aureus DSM 346 | (cfu/plate) | $10^3$ | $10^3$ | $10^3$ | 0 | >1000-fold | n.a.: Not applicable.

From tables 3A and 3B, it can be gathered that the synergistic effect of lithium and sodium ions is shown for both sources. However, the chloride salts show a higher synergistic effect (up to 1 000-fold reduction of bacterial counts) compared to carbonate salts used as a lithium and/or sodium ion source (>20-fold reduction). The synergistic effect reduced bacterial counts up to 1 000-fold.

Example 4: Antimicrobial Surface Activity of Plastic Containing Lithium and Sodium Ions The antimicrobial activity on the surface of a polymer product (moisture content <0.2 wt.-%, based on the total weight of the product) containing lithium and/or sodium ions when in contact with water is shown in Table 4 below. The antimicrobial activities of polymer products surface against the bacterial strain S. aureus DSM 346 were tested according to the Japanese Standard Protocol JIS Z 2801 2000. The results show a synergistic effect of the two ions when added together, compared to their single activity. The bacterial burden is reduced 5-10-fold when both ions are added (the antimicrobial activity increases) instead of only one ion. The negative control was done using plain $CaCO_3$ as filler in the polymer product, i.e. without addition of lithium or sodium carbonate. This polymer surface showed always a bacterial load of >1×10$^6$ cfu/plate.

TABLE 4

A&B: Reduction of bacterial counts on the surface of a polymer product, containing lithium and/or sodium ions.

A

Polymer product containing different amounts of lithium and/or sodium ions added as carbonate salt

| Sodium ions | (ppm) | 0 | 4600 | 0 | 4600 | Synergistic Reduction |
|---|---|---|---|---|---|---|
| Lithium ions | (ppm) | 0 | 0 | 2100 | 2100 | |
| Staphylococcus aureus DSM 346 | (cfu/test item) | >$10^6$ | >$10^6$ | >$10^6$ | 9 × $10^4$ | >10-fold |
| | Antimicrobial activity | n.a. | 0 | 0 | >1.0 | |

B

Polymer product containing different amounts of lithium and/or sodium ions added as carbonate salt

| Sodium ions | (ppm) | 0 | 2300 | 0 | 2300 | Synergistic Reduction |
|---|---|---|---|---|---|---|
| Lithium ions | (ppm) | 0 | 0 | 1050 | 1050 | |
| Staphylococcus aureus DSM 346 | (cfu/test item) | >$10^6$ | >$10^6$ | >$10^6$ | 2 × $10^5$ | >5-fold |
| | Antimicrobial activity | n.a. | 0 | 0 | >0.7 | | n.a.: Not applicable.

From tables 4A and 4B, it can be gathered that S. aureus viable counts could be reduced up to 10-fold by adding both lithium and sodium ions compared to their single addition (synergistic effect).

Example 5: Antimicrobial Surface Activity of Dried Paint Containing Lithium and Sodium Ions The antimicrobial activity on the surface of dried paint containing lithium and/or sodium ions against mould is shown in Table 5 below. The antimicrobial activities against the mould strain A. niger DSM 1957 were tested according to the norm DINE 15457:2007-10. The results show an antimicrobial effect against mould compared to the negative controls. The negative controls were done using both a $CaCO_3$ mineral dispersion and paint without lithium and sodium. The negative controls showed growth already at day 7 and a maximal rating of 4 already after 14 days of incubation. In contrast the lithium and sodium containing paint showed no visible growth after 7 days, a rating of only 1 after 14 days and of 3 after 21 days of incubation. Thus the presence of lithium and sodium ions has reduced fungal growth on dry paint.

TABLE 5

Protection of lithium-/sodium ion-containing painted surfaces from mould.

| | | Dried slurry | Biocide free paint | Sodium and lithium ions containing paint |
|---|---|---|---|---|
| Sodium ions | (ppm)* | 0 | 0 | 72.5 |
| Lithium ions | (ppm)* | 0 | 0 | 36 |
| 7 days after inoculation | (rating 0-4) | 3 | 1 | 0 |
| 14 days after inoculation | (rating 0-4) | 4 | 4 | 1 |
| 21 days after inoculation | (rating 0-4) | 4 | 4 | 3 |

*ppm refers to the final dried product

From table 5, it can be gathered that the paint containing lithium and sodium ions clearly reduced the growth of mould on the painted surface.

Example 6: Preparation of Indoor- and Outdoor Paint Containing Lithium and Sodium Carbonate Coatings of indoor and outdoor dispersion paints were prepared on plastic films with a 0.35 mm thickness. The coatings were air dried for at least two weeks before analysis.

The indoor and outdoor dispersion paints contained 600 ppm lithium ions (from $Li_2CO_3$) and 1880 ppm sodium ions (from $Na_2CO_3$), based on the total weight of the paint.

Untreated indoor dispersion paint consisted of 0.109 wt.-% Calgon N, 0.545 wt.-% Bermocoll Prime 3500, 0.0109 wt.-% Sodium hydroxide, 0.545 wt.-% Byk 038, 0.327 wt.-% Ecodis P50, 10.9 wt.-% TiONA 595, 3.27 wt.-% Optiwhite, 35.4 wt.-% calcium carbonate dry powder, 13.07 wt.-% Mowilith LDM 1871 (53%) and water to 100 wt.-%

Indoor paint with $Li_2CO_3+Na_2CO_3$ consisted of untreated outdoor paint supplemented with 0.317 wt.-% dry $Li_2CO_3$ and 0.433 wt.-% dry $Na_2CO_3$.

Untreated outdoor dispersion paint consisted of 0.3 wt.-% Bermocoll EHM 200, 0.2 wt.-% Amoniak (24%), 0.3 wt.-% Coapur 2025, 0.1 wt.-% Calgon N n, 0.5 wt.-% Borchigen DFN, 1 wt.-% Dowanol DPnB, 1 wt.-% Texanol, 0.5 wt.-% Byk 038, 20 wt.-% TiONA 595, 2 wt.-% Alusil ET, 7 wt.-% Finntalc M20SL-AW, 14 wt.-% calcium carbonate dry powder, 33 wt.-% Mowilith LDM 7717 (46%) and water to 100 wt.-%

Outdoor paint with $Li_2CO_3+Na_2CO_3$ consisted of untreated outdoor paint supplemented with 0.317 wt.-% dry $Li_2CO_3$ and 0.433 wt.-% dry $Na_2CO_3$.

Antimicrobial Surface Activity Test

Fresh bacteria cultures of the bacteria *Staphylococcus aureus* strains DSM 346 were prepared by dilution streaking onto a tryptic soy agar plate (TSA, no. 236950, Becton Dickinson and Company, USA) and incubation for 16 to 20 h at 35° C.

To test the antimicrobial surface activity of coatings, the Japanese Standard Protocol JIS Z 2801 2000 was followed using fresh bacteria prepared as described above. The plating, counting and evaluation were done according to the Japanese Standard Protocol JIS Z 2801 2000 with the following amendments. To confirm results, studies were performed with a single test piece instead of triplicates. For all coated samples, the bacteria were released after incubation from the test item in a petri dish using a sterile Drigalski spatula to massage the test item with medium, instead of using a stomacher bag and massaging the item by hand. Further the test items were not sterilized with 70% ethanol prior analysis.

As described in the Japanese Standard Protocol JIS Z 2801 2000, the bacterial counts are reported as colony forming units per test item (cfu/test item) with 10 cfu/test item as limit of detection (LOD). Thereof the antimicrobial activity (R) of the test items was calculated as described in the Japanese Standard Protocol JIS Z 2801 2000. For it, after 24 h incubation at 35° C., the average number of viable bacteria on the test item (B) and the untreated control (A) are used to calculate the antimicrobial activity (R) using the following formula: $R=\log_{10}(A/B)$. If zero cfu were detected, a value of 10 cfu/test item was used for calculation of the limit of detection of the antimicrobial activity.

The invention claimed is:

1. An antiseptic composition comprising:
   a) at least one inorganic filler material,
   b) one or more source of sodium ions wherein from 20 to 20,000 milligrams per kilogram of the antiseptic composition consists of the source of sodium ions, and
   c) one or more source of lithium ions wherein 20 to 60,000 milligrams per kilogram of the antiseptic composition consists of the source of lithium ions,
   provided that the antiseptic composition comprises a number of moles of lithium ions from the one or more source of lithium ions per mole of sodium ions from the one or more source of sodium ions and the number is from 5 to 10,
   wherein the antiseptic composition comprises <15.0 wt.-% moisture, and
   the antiseptic composition is effective against one or more of (i) a strain of bacteria, (ii) a strain of yeast, and (iii) a strain of mould.

2. The antiseptic composition according to claim 1, wherein the antiseptic composition comprises ≤5.0 wt.-%, moisture.

3. The antiseptic composition according to claim 1, wherein the antiseptic composition comprises ≤1.0 wt.-% moisture.

4. The antiseptic composition according to claim 1, wherein the antiseptic composition comprises ≤0.2 wt.-% moisture.

5. The antiseptic composition according to claim 1, wherein the antiseptic composition comprises from 0.03 to 0.15 wt.-% moisture.

6. The antiseptic composition according to claim 1, having hydrophobic surface properties.

7. The antiseptic composition according to claim 1, wherein the at least one inorganic filler material is selected from the group consisting of ground natural calcium carbonate (GCC), precipitated calcium carbonate (PCC), modified calcium carbonate (MCC), kaolin, kaolinitic clay, calcined kaolinitic clay, talc, calcium sulfate, quartz, attapulgite, montmorillonite, diatomaceous earth, finely divided silica, aluminium oxide, aluminium hydroxide, silicates, pumice, sepiolite, dolomite, mica, titanium dioxide, and any mixture thereof.

8. The antiseptic composition according to claim 1, wherein the at least one inorganic filler material is selected from the group consisting of ground natural calcium carbonate (GCC) from marble, limestone, chalk or any mixture thereof, modified calcium carbonate (MCC), precipitated

TABLE 6

Antimicrobial activity against *S. aureus* of coatings of different dispersion paints.

| Test item | Inoculum | cfu/test item | | | | Antimicrobial activity | |
| --- | --- | --- | --- | --- | --- | --- | --- |
| | | I | II | III | Average | R | LOD |
| untreated indoor paint (before incubation) | S. aureus | 2.3E+05 | 2.4E+05 | 2.5E+05 | 2.4E+05 | N/A | N/A |
| untreated indoor paint | S. aureus | 1.2E+04 | 3.5E+03 | 4.5E+03 | 6.5E+03 | 0.00 | 2.81 |
| indoor paint with $Li_2CO_3 + Na_2CO_3$ | S. aureus | 1.0E+01 | 1.0E+01 | 1.0E+01 | 1.0E+01 | 2.81 | 2.81 |
| Untreated outdoor paint (before incubation) | S. aureus | 2.7E+05 | 2.6E+05 | 2.6E+05 | 2.6E+05 | N/A | N/A |
| Untreated outdoor paint | S. aureus | 5.0E+04 | 5.5E+04 | 4.0E+04 | 4.8E+04 | 0.00 | 3.68 |
| outdoor paint with $Li_2CO_3 + Na_2CO_3$ | S. aureus | 1.0E+01 | 1.0E+01 | 1.0E+01 | 1.0E+01 | 3.68 | 3.68 |

N/A: Not applicable, results from four independent sets of experiments are shown, each set with its own untreated test items as control. For each test item, experiments were performed in triplicates.

calcium carbonate (PCC), dolomite, kaolin, kaolinitic clay, calcined kaolinitic clay, and any mixture thereof.

9. The antiseptic composition according to claim 1, wherein the at least one inorganic filler material is ground natural calcium carbonate (GCC).

10. The antiseptic composition according to claim 1, wherein the at least one inorganic filler material has a volume median diameter $d_{50}$ value from 0.5 to 25.0 μm, measured according to the dry laser diffraction method.

11. The antiseptic composition according to claim 1, wherein the at least one inorganic filler material has a volume median diameter $d_{50}$ value from 0.7 to 5.0 μm, measured according to the dry laser diffraction method.

12. The antiseptic composition according to claim 1, comprising from 20 to 10,000 milligrams of sodium ions per kilogram of the antiseptic composition.

13. The antiseptic composition according to claim 1, comprising from 20 to 30,000 milligrams of lithium ions per kilogram of the antiseptic composition.

14. The antiseptic composition according to claim 1, wherein the one or more source of sodium ions is a carbonate salt, the one or more source of lithium ions is a carbonate salt, or the one or more source of sodium ions is a carbonate salt and the one or more source of lithium ions is a carbonate salt.

15. The antiseptic composition according to claim 1, wherein the antiseptic composition does not comprise any additional biocide.

16. The antiseptic composition according to claim 1, which is prepared by a process comprising the steps of:
   a) providing the at least one inorganic filler material,
   b) providing the one or more source of lithium ions,
   c) providing the one or more source of sodium ions,
   d) combining the at least one inorganic filler material with the one or more source of lithium ions, and
   e) combining the at least one inorganic filler material with the one or more source of sodium ions, wherein
   process steps d) and e) are carried out simultaneously or separately in any order, provided that the antiseptic composition comprises a number of moles of lithium ions from the source of lithium ions per mole of sodium ions from the source of sodium ions and the number is from 1.5 to 10, and
   the antiseptic composition comprises <15.0 wt.-% moisture.

17. The antiseptic composition according to claim 16, wherein the process further comprises step f) of:
   i) dry grinding the mixture of the at least one inorganic filler material, the one or more source of lithium ions and the one or more source of sodium ions obtained during and/or after step d) and e), and/or
   ii) contacting the mixture of the at least one inorganic filler material, the one or more source of lithium ions and the one or more source of sodium ions obtained after step d) and e) with water and/or at least one dispersing agent, or
   iii) contacting the mixture of the at least one inorganic filler material, the one or more source of lithium ions and the one or more source of sodium ions obtained after step d) and e) with an organic polymer composition comprising at least one organic polymer resin being selected from the group consisting of a thermoplast, duroplast, elastomer and mixtures thereof and subjecting the obtained composition to conditions under which it is converted into an antiseptic polymer product.

18. The antiseptic composition according to claim 1, wherein the strain of bacteria is selected from the group consisting of *Escherichia* sp., *Staphylococcus* sp., *Thermus* sp., *Propionibacterium* sp., *Rhodococcus* sp., *Panninobacter* sp., *Caulobacter* sp., *Brevundimonas* sp., *Asticcacaulis* sp., *Sphingomonas* sp., *Rhizobium* sp., *Ensifer* sp., *Bradyrhizobium* sp., *Tepidimonas* sp., *Tepidicella* sp., *Aquabacterium* sp., *Pelomonas* sp., *Alcaligenis* sp., *Achromobacter* sp., *Ralstonia* sp., *Limnobacter* sp., *Massilia* sp., *Hydrogenophaga* sp., *Acidovorax* sp., *Curvibacter* sp., *Delftia* sp., *Rhodoferax* sp., *Alishewanella* sp., *Stenotrophomonas* sp., *Dokdonella* sp., *Methylosinus* sp., *Hyphomicrobium* sp., *Methylosulfomonas* sp., *Methylobacteria* sp., *Pseudomonas* sp. *Enterococcus* sp., *Myroides* sp., *Burkholderia* sp., *Alcaligenes* sp., and any mixture thereof, the strain of mould is selected from the group consisting of *Acremonium* sp., *Alternaria* sp., *Aspergillus* sp., *Cladosporium* sp., *Fusarium* sp., *Mucor* sp., *Penicillium* sp., *Rhizopus* sp., *Stachybotrys* sp., *Trichoderma* sp., *Dematiaceae* sp., *Phoma* sp., *Eurotium* sp., *Scopulariopsis* sp., *Aureobasidium* sp., *Monilia* sp., *Botrytis* sp., *Stemphylium* sp., *Chaetomium* sp., *Mycelia* sp., *Neurospora* sp., *Ulocladium* sp., *Paecilomyces* sp., *Wallemia* sp., *Curvularia* sp., and any mixture thereof, and the strain of yeast is selected from the group consisting of *Saccharomycotina*, *Taphrinomycotina*, *Schizosaccharomycetes*, *Basidiomycota*, *Agaricomycotina*, *Tremellomycetes*, *Pucciniomycotina*, *Microbotryomycetes*, *Candida* sp. such as *Candida albicans*, *Candida tropicalis*, *Candida stellatoidea*, *Candida glabrata*, *Candida krusei*, *Candida guilliermondii*, *Candida viswanathii*, *Candida lusitaniae* and mixtures thereof, *Yarrowia* sp. such as *Yarrowia lipolytica*, *Cryptococcus* sp. such as *Cryptococcus gattii* and *Cryptococcus* neofarmans, *Zygosaccharomyces* sp., *Rhodotorula* sp. such as *Rhodotorula mucilaginosa*, and any mixture thereof.

19. The antiseptic composition according to claim 1, having an antiseptic effect against at least one strain of bacteria selected from the group consisting of *Escherichia coli*, *Staphylococcus aureus*, *Pseudomonas putida*, *Pseudomonas mendocina*, *Pseudomonas oleovorans*, *Pseudomonas fluorescens*, *Pseudomonas alcaligenes*, *Pseudomonas pseudoalcaligenes*, *Pseudomonas entomophila*, *Pseudomonas syringae*, *Methylobacterium extorquens*, *Methylobacterium radiotolerants*, *Methylobacterium dichloromethanicum*, *Methylobacterium organophilu*, *Hyphomicrobium zavarzini*, *Enterococcus faecalis*, *Myroides odoratus*, *Pseudomonas aeruginosa*, *Pseudomonas orizyhabitans*, *Burkholderia cepacia*, *Alcaligenes faecalis* and *Sphingomonas paucimobilis*, and any mixture thereof.

20. The antiseptic composition according to claim 1, wherein the number is from 5 to 8.

21. An antiseptic product comprising the composition according to claim 1.

22. The antiseptic product according to claim 21, which is a non-aqueous slurry, paint, a coating formulation, a cosmetic formulation, a cream, a gel, a fungicidal wall plaster formulation, a film, a plaster, a diaper, a tissue, a plastic product or an adsorbing agent for an aqueous and/or organic fluid.

23. An antiseptic polymer product comprising the composition according to claim 1 and an organic polymer composition comprising at least one organic polymer resin being selected from the group consisting of a thermoplast, duroplast, elastomer, and any mixture thereof.

24. The antiseptic polymer product according to claim 23, wherein the at least one organic polymer resin is selected from the group consisting of halogenated polymer resins, styrenic resins, acrylic resins, polyolefines, polycarbonate resins, polyester resins, polyurethane resins, polyamide resins, biopolymers, copolymers, polyvinyl chlorides, polylactides, acrylonitrile butadiene styrenes, synthetic rubbers, natural rubbers, and any mixture thereof.

* * * * *

UNITED STATES PATENT AND TRADEMARK OFFICE
CERTIFICATE OF CORRECTION

PATENT NO.        : 10,624,348 B2  
APPLICATION NO.   : 15/325236  
DATED             : April 21, 2020  
INVENTOR(S)       : Gane et al.

Page 1 of 1

It is certified that error appears in the above-identified patent and that said Letters Patent is hereby corrected as shown below:

On the Title Page

Assignee Item (73): Delete "OMYA INTERNATIONAL" and insert -- OMYA INTERNATIONAL AG --

Signed and Sealed this  
Ninth Day of June, 2020

Andrei Iancu  
*Director of the United States Patent and Trademark Office*